US007531543B2

(12) United States Patent
Mahaney et al.

(10) Patent No.: US 7,531,543 B2
(45) Date of Patent: May 12, 2009

(54) PHENYLPIPERAZINE CYCLOALKANOL DERIVATIVES AND METHODS OF THEIR USE

(75) Inventors: Paige Erin Mahaney, Pottstown, PA (US); Eugene John Trybulski, Huntingdon Valley, PA (US); Lori Krim Gavrin, Philadelphia, PA (US); An Thien Vu, Pottstown, PA (US)

(73) Assignee: Wyeth, Madison, NJ (US)

( * ) Notice: Subject to any disclaimer, the term of this patent is extended or adjusted under 35 U.S.C. 154(b) by 404 days.

(21) Appl. No.: 10/963,458

(22) Filed: Oct. 12, 2004

(65) Prior Publication Data

US 2005/0143394 A1 Jun. 30, 2005

Related U.S. Application Data

(60) Provisional application No. 60/511,542, filed on Oct. 14, 2003, provisional application No. 60/561,469, filed on Apr. 12, 2004, provisional application No. 60/570,040, filed on May 11, 2004.

(51) Int. Cl.
| | | |
|---|---|---|
| A61K 31/4965 | (2006.01) | |
| C07D 223/00 | (2006.01) | |
| C07D 225/00 | (2006.01) | |
| C07D 241/00 | (2006.01) | |
| C07D 241/02 | (2006.01) | |
| C07D 243/00 | (2006.01) | |
| C07D 245/00 | (2006.01) | |

(52) U.S. Cl. .................. 514/255.04; 540/450; 540/470; 540/484; 540/553; 544/336

(58) Field of Classification Search ................. 544/336; 540/470, 553, 484, 450
See application file for complete search history.

(56) References Cited

U.S. PATENT DOCUMENTS

| | | | | |
|---|---|---|---|---|
| 2,971,955 | A * | 2/1961 | Zaugg et al. | 544/391 |
| 3,454,554 | A | 7/1969 | Biel et al. | 260/239 |
| 4,221,919 | A | 9/1980 | Grimova et al. | 562/465 |
| 4,229,449 | A | 10/1980 | Melloni et al. | 514/239.2 |
| 4,310,524 | A | 1/1982 | Wiech et al. | 514/217 |
| 4,535,186 | A | 8/1985 | Husbands et al. | 564/336 |
| 4,826,844 | A * | 5/1989 | Husbands et al. | 514/252.11 |
| 5,502,047 | A | 3/1996 | Kavey | 514/183 |
| 6,703,389 | B2 | 3/2004 | Wong et al. | 514/239.2 |
| 2002/0107249 | A1 | 8/2002 | Wong et al. | 514/238.5 |
| 2004/0019101 | A1 | 1/2004 | Karlstadt et al. | 514/464 |
| 2004/0143008 | A1 | 7/2004 | Deecher et al. | 514/521 |
| 2004/0152710 | A1 | 8/2004 | Deecher et al. | 514/255.04 |
| 2004/0180879 | A1 | 9/2004 | Deecher et al. | 514/225.8 |
| 2005/0148595 | A1* | 7/2005 | Mahaney | 514/252.12 |

FOREIGN PATENT DOCUMENTS

DE 2556474 C2 8/2004

| | | |
|---|---|---|
| EP | 0 065 757 B1 | 1/1985 |
| EP | 0 310 268 A2 | 4/1989 |
| EP | 0 208 235 B1 | 1/1990 |
| EP | 0 303 961 B1 | 4/1994 |
| EP | 1 266 659 A1 | 12/2002 |
| WO | WO 91/18602 A1 | 12/1991 |
| WO | WO 97/35586 A1 | 10/1997 |
| WO | WO 99/44601 A1 | 9/1999 |
| WO | WO 00/59851 A1 | 10/2000 |
| WO | WO 01/01973 A2 | 1/2001 |
| WO | WO 02/064543 A2 | 8/2002 |
| WO | WO 02/064543 A3 | 8/2002 |
| WO | WO 02/078691 A1 | 10/2002 |
| WO | WO 03/037334 A1 | 5/2003 |
| WO | WO 03/053426 A1 | 7/2003 |
| WO | WO 03/077897 A1 | 9/2003 |
| WO | WO 2004/016272 A1 | 2/2004 |
| WO | 2004/035035 A1 | 4/2004 |
| WO | 2004/035036 A1 | 4/2004 |
| WO | 2004/035058 A1 | 4/2004 |

OTHER PUBLICATIONS

Zaugg, et al., Tertiary Carbinols of the piperazine Series. IV. Products Derived from the Nucleophilic Condensations of 2-Methylpyrazine and 1-Methyl-4-phenylacetylpiperazine, J. of the American Chem. Soc., 80, 2773-4 (1958).*
Cryan, J., et al., 5-HT1A and Beyond: The Role of Serotonin and its Receptors in Depression and the Antidepressant Response, Hum. Psychopharmacol. Clin. Exp. 15, 113-135 (2000).*
U.S. Appl. No. 60/557,651, filed Mar. 30, 2004, Kim et al.
U.S. Appl. No. 60/557,831, filed Mar. 30, 2004, Kim et al.
U.S. Appl. No. 60/569,863, filed May 11, 2004, Kim et al.
U.S. Appl. No. 60/569,861, filed May 11, 2004, Vu.
U.S. Appl. No. 10/962,897, filed Oct. 12, 2004, Deecher et al.
U.S. Appl. No. 10/962,881, filed Oct. 12, 2004, Mahaney.
U.S. Appl. No. 10/963,064, filed Oct. 12, 2004, Trybulski et al.
U.S. Appl. No. 10/963,111, filed Oct. 12, 2004, Trybulski et al.
U.S. Appl. No. 10/962,880, filed Oct. 12, 2004, Trybulski et al.
U.S. Appl. No. 10/962,971, filed Oct. 12, 2004, Mahaney et al.
U.S. Appl. No. 10/962,899, filed Oct. 12, 2004, Mahaney et al.

(Continued)

Primary Examiner—James O Wilson
Assistant Examiner—Erich A Leeser
(74) Attorney, Agent, or Firm—Thomas C. McKenzie

(57) ABSTRACT

The present invention is directed to phenylpiperazine cycloalkanol derivatives, compositions containing these derivatives, and methods of their use for the prevention and treatment of conditions ameliorated by monoamine reuptake including, inter alia, vasomotor symptoms (VMS), sexual dysfunction, gastrointestinal and genitourinary disorders, chronic fatigue syndrome, fibromylagia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

20 Claims, 2 Drawing Sheets

OTHER PUBLICATIONS

Clinical Trial: "Phase III Randomized Study of Medroxyprogesterone Versus Venlafaxine in Women With Symptomatic Hot Flashes", www.clinicaltrials.gov sponsored by the National Institutes of Health, Study ID Nos. CDR0000069217; NCCTG-N99C7; NCI-P02-0204, 2003, 6 pages.

Acs, N. et al., "Estrogen improves impaired musculocutaneous vascular adrenergic reactivity in pharmacologically ovariectomized rats: a potential peripheral mechanism for hot flashes?", *Endocrinology*, 2001 15: 68-73.

Barlow, D. H., "Venlafaxine for hot flushes," *Lancet*, Dec. 16, 2000, 356(9247): 2025-2026.

Barton, D. et al., "Hot Flashes—Aetiology and Management," *Drugs and Aging*, 2001, 18(8): 597-606.

Berendsen, H. H. G., "Hot Flushes and serotonin," *Journal of the British Menopause Society*, Mar. 2002, 8(1): 30-34.

Berendsen, H. H. G., "Effect of tibolone and raloxifene on the tail temperature of oestrogen-deficient rats," *European Journal of Pharmacology*, 2001, 419(1): 47-54.

Berendsen, H. H. G., "The role of serotonin in hot flushes," *Maturitas*, 2000, 36(3): 155-164.

Bundgaard, H., "Means to enhance penetration; Prodrugs as a means to improve the delivery of peptide drugs," *Advanced Drug Deliver Reviews*, 1992, 8, 1-38.

Bundgaard, H. et al., "Glycolamide Esters as Biolabile Prodrugs of Carboxylic Acid Agents: Synthesis, Stability, Bioconversion, and Physicochemical Properties," *J. of Pharmaceutical Sciences*, Apr. 1988, 77(4):285-298.

Casper, R. F. et al., "Neuroendocrinology of menopausal flushes: an hypothesis of flush mechanism," *Clinical Endocrinology*, 1985, 22: 293-312.

Fink, G. et al., "Oestrogen and mental state," *Nature*, 1996, 383(6598): 306.

Freedman, R. R. et al., "Clonidine raises the sweating threshold in symptomatic but not asymptomatic postmenopausal women," *Fertility & Sterility*, 2000, 74(1): 20-3.

Freedman, R. R., "Physiology of hot flashes," *American Journal of Human Biology*, 2001, 13: 453-464.

French, N., "$\alpha_2$-Adrenoceptors and $I_2$ sites in the mammalian central nervous system," *Pharmacol. Ther.*, 1995, 68(2):175-208.

Janowsky, D. S. et al., "Desipramine: an overview," *Journal of Clinical Psychiatry*, 1984, 45(10 Pt 2): 3-9.

Katovich, M. J. et al., "Mechanisms Mediating the Thermal Response to Morphine Withdrawal in Rats," *Proceedings of the Society for Experimental Biology & Medicine*, 1990, 193(2): 129-35.

Katovich, M. J. et al., "Alpha-adrenergic mediation of the tail skin temperature response to naloxone in morphine-dependent rats," *Brain Research*, 1987, 426: 55-61.

Krämer et al., In: Murphy et al., $3^{rd}$ *Int'l Symposium on Recent Advances in Urological Cancer Diagnosis and Treatment-Proceedings*, Paris, France: SCI: 3-7 1992.

Krogsgaard-Larsen, et al., (ed). *Design and Application of Prodrugs, Textbook of Drug Design and Development*, Chapter 5, 113-191, 1991.

Kronenberg, F. et al., "Thermoregulatory Physiology of Menopausal Hot Flashes: A Review," *Can. J. Physiol. Pharmacol.*, 1987, 65:1312-1324.

Loprinzi, C.L. et al., "Venlafaxine in management of hot flashes in survivors of breast cancer: a randomized controlled trial," *Lancet*, Dec. 16, 2000, 356(9247): 2059-2063.

Loprinizi, C. L. et al. "Pilot Evaluation of Venlafaxine Hydrochloride for the Therapy of Hot Flashes in Cancer Survivors," *Journal of Clinical Oncology*, Jul. 1998, 16(7): 2377-2381.

Mackinnon et al., "$\alpha_2$-Adrenoceptors: more subtypes but fewer functional differences," *TIPS*, 1994, 15: 119-123.

Merchenthaler et al., "The effect of estrogens and antiestrogens in a rat model for hot flush," *Maturitas*, 1998, 30(3): 307-316.

Morin, S. M., "Atomoxetine Selectivity Induces Fos Expression in the Rat Prefrontal Cortex," Presented at Society for Neuroscience Annual Meeting (SFN); Nov. 2-7, 2002, Orlando, FL.

Pacholczyk, T. et al., "Expression cloning of a cocaine-and antidepressant-sensitive human noradrenaline transporter," *Nature*, 1991, 350(6316): 350-4.

Panek, D.U. et al., "Effect of continuous intraventricular estrogen or catechol estrogen treatment on catecholamine turnover in various brain regions," *J. Pharmacol. Exp. Ther.*, 1986, 236(3), 646-652.

Prasad, P.D., et al., "Functional expression of the plasma membrane serotonin transporter but not the vesicular monoamine transporter in human placental trophoblasts and choriocarcinoma cells," *Placenta*, 1996, 17(4): 201-7.

Quella, S. K. et al., "Pilot evaluation of Venlafaxine for the treatment of hot flashes in men undergoing androgen ablation therapy for prostate cancer," *The Journal of Urology*, Jul. 1999, 162: 98-102.

Reneric, J-Ph. et al., "Idazoxan and 8-OH-DPAT modify the behavioral effects induced by either NA, or 5-HT, or dual NA/5-HT reuptake inhibition in the rat forced swimming test," *Nueropsychopharmacology*, Apr. 2001, 24(4): 379-390.

Rosenberg, J. et al., "Hypothesis: pathogenesis of postmenopausal hot flush," *Medical Hypotheses*, 1991, 35: 349-350.

Shaw, C. R., "The perimenopausal hot flash: epidemiology, physiology, and treatment," *Nurse Practitioner*, Mar. 1997, 22: 55-56, 61-66.

Stearns, V. et al., "Hot flushes," *Lancet*, Dec. 7, 2002, 360(9348): 1851-1861.

Stearns,V. et al., "Paroxetine controlled release in the treatment of menopausal hot flashes," *JAMA*, 2003, 289:2827-2834.

Stearns, V. et al., "A pilot trial assessing the efficacy of paroxetine hydrochloride (Paxil) in controlling hot flashes in breast cancer survivors," *Ann Oncol.*, 2000, 11:17-22.

Waldinger et al., "Treatment of hot flushes with mirtazapine: four case reports," *Maturitas*, 2000, 36(3): 165-168.

Wilen, S.H. *Tables of Resolving Agents and Optical Resolutions*, pp. 268-298, E.L. Eliel, Ed., University of Notre Dame Press, Notre Dame, IN 1972.

Wilen, S.H., et al., "Strategies in optical resolutions," *Tetrahedron*, 33:2725-2736, 1977.

Zhang, W. et al., "Synergistic Effects of Olanzapine and Other Antipsychotic Agents in Combination with Fluoxetine on Norepinephrine and Dopamine Release in Rat Prefrontal Cortex," *Neuropsychopharmacology*, 2000, 23(3): 250-262.

Bundgaard (ed.), *Design of Prodrugs*, Elsevier (1985), Ch. 1 (pp. 1-92), Ch. 4 (pp. 157-176), Ch. 5 (pp. 177-198), and Ch. 6 (pp. 199-241).

Widder, et al. (ed.), *Methods in Enzymology*, vol. 112, Academic Press (1985), pp. 309-396.

Higuchi and Stella (eds.), *Prodrugs as Novel Drug Delivery Systems*, American Chemical Society (1975), pp. 1-115 and 196-223.

Freedman, R. R. et al., "$\alpha 2$-Adrenergic mechanism in menopausal hot flushes," *Obstet Gynecol*, 1990, 76:573-578.

Brück, K. et al., "Adaptive changes in thermoregulation and their neuropharmacological basis" In: Schönbaum E. et al. (eds.). *Thermoregulation: Physiology and Biochemistry*, New York, Pergamon Press, (1991) pp. 255-307.

Ahmar, M. et al., "Enzymatic resolution of methyl 2-alkyl-2-arylacetates" *Tetrahedron Lett.*, 1989, 30(50): 7053-7056.

Campaigne, E. et al., "Benzo[β]thiophene Derivatives. XXVII. 5-Methoxy-6-halo-3-b-acetamidoethylbenzo[b]thiophenes, Blocked Analogs of Melatonin," *J. Heterocyclic Chem.* 1983, 20, 1697-1703.

Harrison, I. et al., "Nonsteroidal antiinflammatory agents. I. 6-substituted 2-naphthylacetic acids," *J. Med. Chem.* 1970, 13(2), 203-5.

Moon, S. et al., "An Efficient Conversion of Chiral α-Amino Acids to Enantiomerically Pure 3-Amino Cyclic Amines," *Synth. Commun.* 1998, 28(21), 3919-3926.

Baker, W.et al., "Nonpeptide renin inhibitors employing a novel 3-aza(or oxa)-2,4-dialkyl glutaric acid moiety as a P2/P3 amide bond replacement," *J. Med. Chem.* 1992, 35 (10), 1722-1734.

Ley, S.V. et al., "Use of polymer supported reagents for clean multistep organic synthesis: preparation of amines and amine derivatives from alcohols for use in compound library generation," *J. Chem. Soc. Perkin Trans. I*; 15; 1998; 2239-2242.

Manov et al., "Solid-Phase Synthesis of Polyamine Spider Toxins and Correlation with the Natural Products by HPLC-MS/MS," *Helvetica Chimica Acta*, 2002, 85(9):2827-2846.

Monguzzi, R. et al., "Synthesis of new α-hydrazinoarylacetic acids and derivatives," *Farmaco, Edizione Scientifica*, 1976, 31(8), 549-60.

*Remington's Pharmaceutical Sciences*, 17th edition, ed. Alfonoso R. Gennaro, Mack Publishing Company, Easton, PA, 1985.

Eliel, E.L. *Stereochemistry of Carbon Compounds*, McGraw-Hill, NY, 1962.

Jacques, et al., *Enantiomers, Racemates and Resolutions*, Wiley Interscience, New York, 1981.

Greene, T.W. and Wuts, P.G.M., *Protective Groups in Organic Synthesis* 2d. Ed., Wiley & Sons, 1991.

Leventhal et al. "Differential and Synergistic Effects of Selective Norepinephrine and Serotonin Reuptake Inhibitors in Rodent Models of Pain." The Journal of Pharmacology and Experimental Therapeutics vol. 320, No. 3 pp. 1178-1185.

\* cited by examiner

PHENYLPIPERAZINE CYCLOALKANOL DERIVATIVES AND METHODS OF THEIR USE

CROSS REFERENCE TO RELATED APPLICATIONS

This application claims the benefit of U.S. application Nos. 60/511,542 filed Oct. 14, 2003, 60/561,469 filed Apr. 12, 2004, and 60/570,040 filed May 11, 2004, the entire disclosures of which are herein incorporated by reference.

FIELD OF THE INVENTION

The present invention relates to phenylpiperazine cycloalkanol derivatives, compositions containing these derivatives, and methods of their use for the prevention and treatment of conditions ameliorated by monoamine reuptake including, inter alia, vasomotor symptoms (VMS), sexual dysfunction, gastrointestinal and genitourinary disorders, chronic fatigue syndrome, fibromyalgia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

BACKGROUND OF THE INVENTION

Vasomotor symptoms (VMS), referred to as hot flushes and night sweats, are the most common symptoms associated with menopause, occurring in 60% to 80% of all women following natural or surgically-induced menopause. VMS are likely to be an adaptive response of the central nervous system (CNS) to declining sex steroids. To date, the most effective therapies for VMS are hormone-based treatments, including estrogens and/or some progestins. Hormonal treatments are very effective at alleviating VMS, but they are not appropriate for all women. It is well recognized that VMS are caused by fluctuations of sex steroid levels and can be disruptive and disabling in both males and females. A hot flush can last up to thirty minutes and vary in their frequency from several times a week to multiple occurrences per day. The patient experiences a hot flash as a sudden feeling of heat that spreads quickly from the face to the chest and back and then over the rest of the body. It is usually accompanied by outbreaks of profuse sweating. It may sometimes occur several times an hour, and it often occurs at night. Hot flushes and outbreaks of sweats occurring during the night can cause sleep deprivation. Psychological and emotional symptoms observed, such as nervousness, fatigue, irritability, insomnia, depression, memory loss, headache, anxiety, nervousness or inability to concentrate are considered to be caused by the sleep deprivation following hot flush and night sweats (Kramer et al., In: Murphy et al., 3$^{rd}$ Int'l Symposium on Recent Advances in Urological Cancer Diagnosis and Treatment-Proceedings, Paris, France: SCI: 3-7 (1992)).

Hot flushes may be even more severe in women treated for breast cancer for several reasons: 1) many survivors of breast cancer are given tamoxifen, the most prevalent side effect of which is hot flush, 2) many women treated for breast cancer undergo premature menopause from chemotherapy, 3) women with a history of breast cancer have generally been denied estrogen therapy because of concerns about potential recurrence of breast cancer (Loprinzi, et al., Lancet, 2000, 356(9247): 2059-2063).

Men also experience hot flushes following steroid hormone (androgen) withdrawal. This is true in cases of age-associated androgen decline (Katovich, et al., Proceedings of the Society for Experimental Biology & Medicine, 1990, 193 (2): 129-35) as well as in extreme cases of hormone deprivation associated with treatments for prostate cancer (Berendsen, et al., European Journal of Pharmacology, 2001, 419(1): 47-54. As many as one-third of these patients will experience persistent and frequent symptoms severe enough to cause significant discomfort and inconvenience.

The precise mechanism of these symptoms is unknown but generally is thought to represent disturbances to normal homeostatic mechanisms controlling thermoregulation and vasomotor activity (Kronenberg et al., "Thermoregulatory Physiology of Menopausal Hot Flashes: A Review," Can. J. Physiol. Pharmacol., 1987, 65:1312-1324).

The fact that estrogen treatment (e.g. estrogen replacement therapy) relieves the symptoms establishes the link between these symptoms and an estrogen deficiency. For example, the menopausal stage of life is associated with a wide range of other acute symptoms as described above and these symptoms are generally estrogen responsive.

It has been suggested that estrogens may stimulate the activity of both the norepinephrine (NE) and/or serotonin (5-HT) systems (J. Pharmacology & Experimental Therapeutics, 1986, 236(3) 646-652). It is hypothesized that estrogens modulate NE and 5-HT levels providing homeostasis in the thermoregulatory center of the hypothalamus. The descending pathways from the hypothalamus via brainstem/spinal cord and the adrenals to the skin are involved in maintaining normal skin temperature. The action of NE and 5-HT reuptake inhibitors is known to impinge on both the CNS and peripheral nervous system (PNS). The pathophysiology of VMS is mediated by both central and peripheral mechanisms and, therefore, the interplay between the CNS and PNS may account for the efficacy of dual acting SRI/NRIs in the treatment of thermoregulatory dysfunction. In fact, the physiological aspects and the CNS/PNS involvement in VMS may account for the lower doses proposed to treat VMS (Loprinzi, et al. Lancet, 2000, 356:2059-2063; Stearns et al., JAMA, 2003, 289:2827-2834) compared to doses used to treat the behavioral aspects of depression. The interplay of the CNS/PNS in the pathophysiology of VMS and the presented data within this document were used to support the claims that the norepinephrine system could be targeted to treat VMS.

Although VMS are most commonly treated by hormone therapy (orally, transdermally, or via an implant), some patients cannot tolerate estrogen treatment (Berendsen, Maturitas, 2000, 36(3): 155-164, Fink et al., Nature, 1996, 383(6598): 306). In addition, hormone replacement therapy is usually not recommended for women or men with or at risk for hormonally sensitive cancers (e.g. breast or prostate cancer). Thus, non-hormonal therapies (e.g. fluoxetine, paroxetine [SRIs] and clonidine) are being evaluated clinically. WO9944601 discloses a method for decreasing hot flushes in a human female by administering fluoxetine. Other options have been studied for the treatment of hot flashes, including steroids, alpha-adrenergic agonists, and beta-blockers, with varying degree of success (Waldinger et al., Maturitas, 2000, 36(3): 165-168).

It has been reported that $\alpha_2$-adrenergic receptors play a role in thermoregulatory dysfunctions (Freedman et al., Fertility & Sterility, 2000, 74(1): 20-3). These receptors are located both pre- and post-synaptically and mediate an inhibitory role in the central and peripheral nervous system. There are four distinct subtypes of the adrenergic$_{\alpha 2}$ receptors, i.e., are $\alpha_{2A}$, $\alpha_{2B}$, $\alpha_{2C}$ and $\alpha_{2D}$ (Mackinnon et al., TIPS, 1994, 15: 119;

French, *Pharmacol. Ther.,* 1995, 68: 175). It has been reported that a non-select $\alpha_2$-adrenoceptor antagonist, yohimbine, induces a flush and an $\alpha_2$-adrenergic receptor agonist, clonidine, alleviates the yohimbine effect (Katovich, et al., *Proceedings of the Society for Experimental Biology & Medicine,* 1990, 193(2): 129-35, Freedman et al., *Fertility & Sterility,* 2000, 74(1): 20-3). Clonidine has been used to treat hot flush. However, using such treatment is associated with a number of undesired side effects caused by high doses necessary to abate hot flash described herein and known in the related arts.

Given the complex multifaceted nature of thermoregulation and the interplay between the CNS and PNS in maintaining thermoregulatory homeostasis, multiple therapies and approaches can be developed to target vasomotor symptoms. The present invention focuses on novel compounds and compositions containing these compounds directed to these and other important uses.

SUMMARY OF THE INVENTION

The present invention is directed to phenylpiperazine cycloalkanol derivatives, compositions containing these derivatives, and methods of their use for the prevention and treatment of conditions ameliorated by monoamine reuptake including, inter alia, vasomotor symptoms (VMS), sexual dysfunction, gastrointestinal and genitourinary disorders, chronic fatigue syndrome, fibromyalgia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

In one embodiment, the present invention is directed to compounds of formula I:

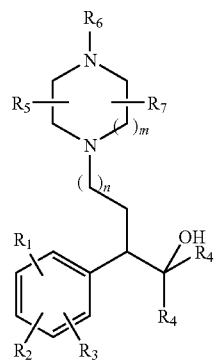

or a pharmaceutically acceptable salt thereof;
wherein:
$R^1$, $R^2$ and $R^3$ are, independently, H, OH, alkyl, alkoxy, alkanoyloxy, $CF_3$, halo, or methylenedioxy;
$R^4$, taken together with the carbon atom to which they are attached, form a cycloalkyl ring of 4 to 8 carbon atoms;
$R^5$, $R^6$, and $R^7$ are, independently, H or ($C_1$-$C_4$)alkyl, provided that at least one of $R^5$, $R^6$, and $R^7$ is other than H;
or $R^5$ and $R^6$, together with the nitrogen atom to which $R^6$ is attached, form a heterocyclic ring;
m is 1, 2, or 3; and
n is 0, 1, 2, or 3.

In another embodiment, the present invention is directed to methods for treating or preventing vasomotor symptoms in a subject in need thereof, comprising the step of:
administering to said subject an effective amount of at least one compound of formula I or pharmaceutically acceptable salt thereof.

In yet another embodiment, the present invention is directed to methods for treating or preventing a depression disorder in a subject in need thereof, comprising the step of:
administering to said subject an effective amount of at least one compound of formula I or pharmaceutically acceptable salt thereof.

In yet other embodiments, the present invention is directed to methods for treating or preventing sexual dysfunction in a subject in need thereof, comprising the step of:
administering to said subject an effective amount of at least one compound of formula I or pharmaceutically acceptable salt thereof.

In further embodiments, the present invention is directed to methods for treating or preventing pain in a subject in need thereof, comprising the step of:
administering to said subject an effective amount of at least one compound of formula I or pharmaceutically acceptable salt thereof.

BRIEF DESCRIPTION OF THE DRAWINGS

The invention can be more fully understood from the following detailed description and the accompanying drawings that form a part of this application.

DETAILED DESCRIPTION OF THE INVENTION

Figure 1:
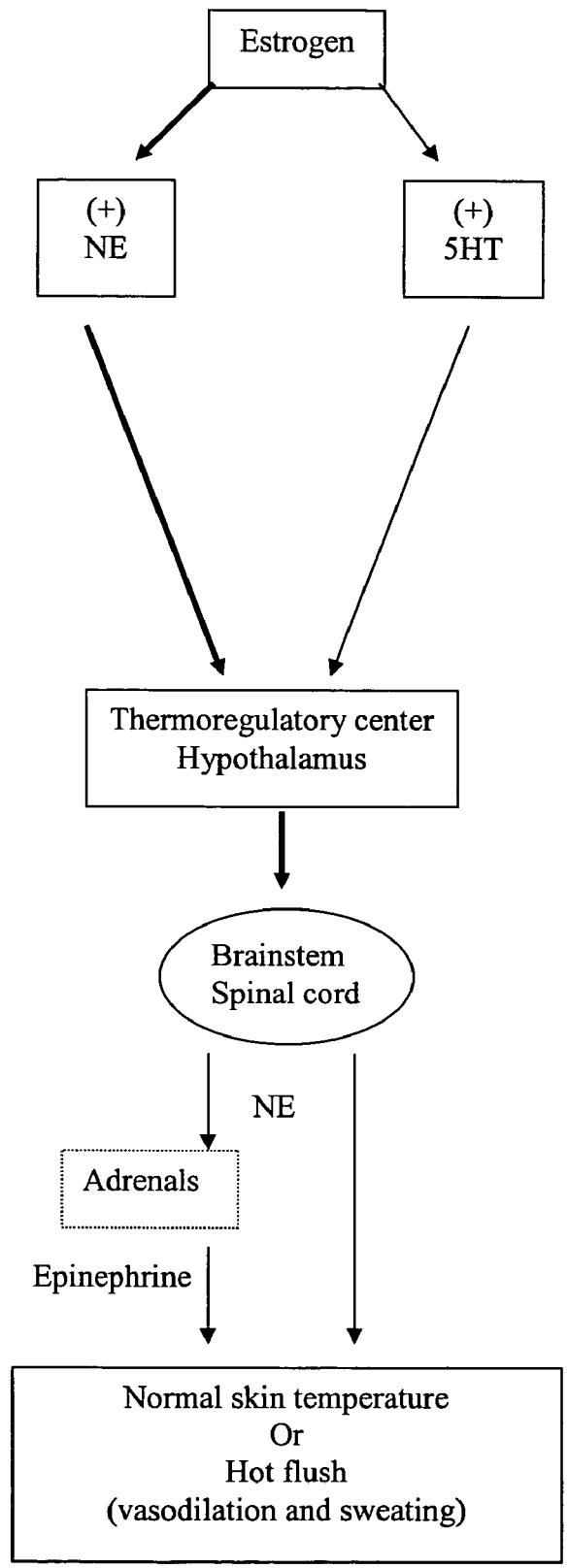
FIG. 1 is an overview of estrogen action on norepinephrine/serotonin mediated thermoregulation.

The present invention is directed to phenylpiperazine cycloalkanol derivatives, compositions containing these derivatives, and methods of their use for the prevention and treatment of conditions ameliorated by monoamine reuptake including, inter alia, vasomotor symptoms (VMS), sexual dysfunction, gastrointestinal and genitourinary disorders, chronic fatigue syndrome, fibromyalgia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

The following definitions are provided for the full understanding of terms and abbreviations used in this specification.

As used herein and in the appended claims, the singular forms "a," "an," and "the" include the plural reference unless the context clearly indicates otherwise. Thus, for example, a reference to "an antagonist" includes a plurality of such antagonists, and a reference to "a compound" is a reference to one or more compounds and equivalents thereof known to those skilled in the art, and so forth.

The abbreviations in the specification correspond to units of measure, techniques, properties, or compounds as follows: "min" means minutes, "h" means hour(s), "μL" means microliter(s), "mL" means milliliter(s), "mM" means millimolar, "M" means molar, "mmole" means millimole(s), "cm" means centimeters, "SEM" means standard error of the mean and "IU" means International Units. "Δ° C." and Δ "$ED_{50}$ value"

means dose which results in 50% alleviation of the observed condition or effect (50% mean maximum endpoint).

"Norepinephrine transporter" is abbreviated NET.
"Human norepinephrine transporter" is abbreviated hNET.
"Serotonin transporter" is abbreviated SERT.
"Human serotonin transporter" is abbreviated hSERT.
"Norepinephrine reuptake inhibitor" is abbreviated NRI.
"Selective norepinephrine reuptake inhibitor" is abbreviated SNRI.
"Serotonin reuptake inhibitor" is abbreviated SRI.
"Selective serotonin reuptake inhibitor" is abbreviated SSRI.
"Norepinephrine" is abbreviated NE.
"Serotonin is abbreviated 5-HT.
"Subcutaneous" is abbreviated sc.
"Intraperitoneal" is abbreviated ip.
"Oral" is abbreviated po.

In the context of this disclosure, a number of terms shall be utilized. The term "treatment" as used herein includes preventative (e.g., prophylactic), curative or palliative treatment and "treating" as used herein also includes preventative, curative and palliative treatment.

The term "effective amount," as used herein, refers to an amount effective, at dosages, and for periods of time necessary, to achieve the desired result with respect to prevention or treatment of vasomotor symptoms, depression disorders, sexual dysfunction, or pain. In particular with respect to vasomotor symptoms, "effective amount" refers to the amount of compound or composition of compounds that would increase norepinephrine levels to compensate in part or total for the lack of steroid availability in subjects subject afflicted with a vasomotor symptom. Varying hormone levels will influence the amount of compound required in the present invention. For example, the pre-menopausal state may require a lower level of compound due to higher hormone levels than the peri-menopausal state.

It will be appreciated that the effective amount of components of the present invention will vary from patient to patient not only with the particular compound, component or composition selected, the route of administration, and the ability of the components (alone or in combination with one or more combination drugs) to elicit a desired response in the individual, but also with factors such as the disease state or severity of the condition to be alleviated, hormone levels, age, sex, weight of the individual, the state of being of the patient, and the severity of the pathological condition being treated, concurrent medication or special diets then being followed by the particular patient, and other factors which those skilled in the art will recognize, with the appropriate dosage ultimately being at the discretion of the attendant physician. Dosage regimens may be adjusted to provide the improved therapeutic response. An effective amount is also one in which any toxic or detrimental effects of the components are outweighed by the therapeutically beneficial effects.

Preferably, the compounds of the present invention are administered at a dosage and for a time such that the number of hot flushes is reduced as compared to the number of hot flushes prior to the start of treatment. Such treatment can also be beneficial to reduce the overall severity or intensity distribution of any hot flushes still experienced, as compared to the severity of hot flushes prior to the start of the treatment. With respect to depression disorders, sexual dysfunction, and pain, the compounds of the present invention are administered at a dosage and for a time such that there is the prevention, alleviation, or elimination of the symptom or condition.

For example, for an afflicted patient, compounds of formula I may be administered, preferably, at a dosage of from about 0.1 mg/day to about 200 mg/day, more preferably from about 1 mg/day to about 100 mg/day and most preferably from about 1 mg/day to 50 mg/day for a time sufficient to reduce and/or substantially eliminate the number and/or severity of hot flushes or symptom or condition of the depression disorder, sexual dysfunction, or pain.

The terms "component," "composition of compounds," "compound," "drug," or "pharmacologically active agent" or "active agent" or "medicament" are used interchangeably herein to refer to a compound or compounds or composition of matter which, when administered to a subject (human or animal) induces a desired pharmacological and/or physiologic effect by local and/or systemic action.

The terms "component", "drug" or "pharmacologically active agent" or "active agent" or "medicament" are used interchangeably herein to refer to a compound or compounds or composition of matter which, when administered to an organism (human or animal) induces a desired pharmacologic and/or physiologic effect by local and/or systemic action.

The term "modulation" refers to the capacity to either enhance or inhibit a functional property of a biological activity or process, for example, receptor binding or signaling activity. Such enhancement or inhibition may be contingent on the occurrence of a specific event, such as activation of a signal transduction pathway and/or may be manifest only in particular cell types. The modulator is intended to comprise any compound, e.g., antibody, small molecule, peptide, oligopeptide, polypeptide, or protein, preferably small molecule, or peptide.

As used herein, the term "inhibitor" refers to any agent that inhibits, suppresses, represses, or decreases a specific activity, such as serotonin reuptake activity or the norepinephrine reuptake activity.

The term "inhibitor" is intended to comprise any compound, e.g., antibody, small molecule, peptide, oligopeptide, polypeptide, or protein, preferably small molecule or peptide, that exhibits a partial, complete, competitive and/or inhibitory effect on mammalian, preferably the human norepinephrine reuptake or both serotonin reuptake and the norepinephrine reuptake, thus diminishing or blocking, preferably diminishing, some or all of the biological effects of endogenous norepinephrine reuptake or of both serotonin reuptake and the norepinephrine reuptake.

Within the present invention, the compounds of formula I may be prepared in the form of pharmaceutically acceptable salts. As used herein, the term "pharmaceutically acceptable salts" refers to salts prepared from pharmaceutically acceptable non-toxic acids, including inorganic salts, and organic salts. Suitable non-organic salts include inorganic and organic acids such as acetic, benzenesulfonic, benzoic, camphorsulfonic, citric, ethenesulfonic, fumaric, gluconic, glutamic, hydrobromic, hydrochloric, isethionic, lactic, malic, maleic, mandelic, methanesulfonic, mucic, nitric, pamoic, pantothenic, phosphoric, succinic, sulfuric, tartaric acid, p-toluenesulfonic and the like. Particularly preferred are hydrochloric, hydrobromic, phosphoric, and sulfuric acids, and most preferably is the hydrochloride salt.

"Administering," as used herein, means either directly administering a compound or composition of the present invention, or administering a prodrug, derivative or analog which will form an equivalent amount of the active compound or substance within the body.

The term "subject" or "patient" refers to an animal including the human species that is treatable with the compositions, and/or methods of the present invention. The term "subject" or "subjects" is intended to refer to both the male and female gender unless one gender is specifically indicated. Accordingly, the term "patient" comprises any mammal which may benefit from treatment or prevention of vasomotor symptoms, depression disorders, sexual dysfunction, or pain, such as a human, especially if the mammal is female, either in the pre-menopausal, peri-menopausal, or post-menopausal period. Furthermore, the term patient includes female animals including humans and, among humans, not only women of advanced age who have passed through menopause but also women who have undergone hysterectomy or for some other reason have suppressed estrogen production, such as those who have undergone long-term administration of corticosteroids, suffer from Cushing's syndrome or have gonadal dysgenesis. However, the term "patient" is not intended to be limited to a woman.

The terms "premature menopause" or "artificial menopause" refer to ovarian failure of unknown cause that may occur before age 40. It may be associated with smoking, living at high altitude, or poor nutritional status. Artificial menopause may result from oophorectomy, chemotherapy, radiation of the pelvis, or any process that impairs ovarian blood supply.

The term "pre-menopausal" means before the menopause, the term "peri-menopausal" means during the menopause and the term "post-menopausal" means after the menopause. "Ovariectomy" means removal of an ovary or ovaries and can be effected according to Merchenthaler et al., *Maturitas*, 1998, 30(3): 307-316.

"Side effect" refers to a consequence other than the one(s) for which an agent or measure is used, as the adverse effects produced by a drug, especially on a tissue or organ system other then the one sought to be benefited by its administration. In the case, for example, of high doses of NRIs or NRI/SRI compounds alone, the term "side effect" may refer to such conditions as, for example, vomiting, nausea, sweating, and flushes (Janowsky, et al., *Journal of Clinical Psychiatry*, 1984, 45(10 Pt 2): 3-9).

"Alkyl," as used herein, refers to an aliphatic hydrocarbon chain of 1 to about 20 carbon atoms, preferably 1 to 10 carbon atoms, more preferably, 1 to 6 carbon atoms, and even more preferably, 1 to 4 carbon atoms and includes straight and branched chains such as methyl, ethyl, n-propyl, isopropyl, n-butyl, isobutyl, sec-butyl, t-butyl, n-pentyl, isopentyl, neopentyl, n-hexyl, and isohexyl. Lower alkyl refers to alkyl having 1 to 4 carbon atoms.

"Alkoxy," as used herein, refers to the group R—O— where R is an alkyl group of 1 to 6 carbon atoms.

"Alkoxycarbonyl," as used herein, refers to the group R—O—C(=O)— where R is an alkyl group of 1 to 6 carbon atoms.

"Alkanoyl," as used herein, refers to the group R—C(=O)— where R is an alkyl group of 1 to 6 carbon atoms.

"Alkanoyloxy," as used herein, refers to the group R—C(=O)—O— where R is an alkyl group of 1 to 6 carbon atoms.

"Alkylaminocarbonyl," as used herein, refers to the group R—NH—C(=O)— where R is an alkyl group of 1 to 6 carbon atoms.

"Alkylcarbonylamino," as used herein, refers to the group R—C(=O)—NH where R is an alkyl group of 1 to 6 carbon atoms.

"Alkenyl" or "olefinic," as used herein, refers to an alkyl group of at least two carbon atoms having one or more double bonds, wherein alkyl is as defined herein. Alkenyl groups can be optionally substituted.

"Alkynyl," as used herein, refers to an alkyl group of at least two carbon atoms having one or more triple bonds, wherein alkyl is as defined herein. Alkynyl groups can be optionally substituted.

"Aryl" as used herein, refers to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons being preferred. Non-limiting examples include, for example, phenyl, naphthyl, anthracenyl, and phenanthrenyl.

"Heteroaryl," as used herein, refers to an optionally substituted, mono-, di-, tri-, or other multicyclic aromatic ring system that includes at least one, and preferably from 1 to about 4 sulfur, oxygen, or nitrogen heteroatom ring members. Heteroaryl groups can have, for example, from about 3 to about 50 carbon atoms (and all combinations and subcombinations of ranges and specific numbers of carbon atoms therein), with from about 4 to about 10 carbons being preferred. Non-limiting examples of heteroaryl groups include, for example, pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl.

"Heterocyclic ring," as used herein, refers to a stable 5- to 7-membered monocyclic or bicyclic or 7- to 10-membered bicyclic heterocyclic ring that is saturated, partially unsaturated or unsaturated (aromatic), and which contains carbon atoms and from 1 to 4 heteroatoms independently selected from the group consisting of N, O and S and including any bicyclic group in which any of the above defined heterocyclic rings is fused to a benzene ring. The nitrogen and sulfur heteroatoms may optionally be oxidized. The heterocyclic ring may be attached to its pendant group at any heteroatom or carbon atom that results in a stable structure. The heterocyclic rings described herein may be substituted on carbon or on a nitrogen atom if the resulting compound is stable. If specifically noted, a nitrogen atom in the heterocycle may optionally be quaternized. It is preferred that when the total number of S and O atoms in the heterocycle exceeds one, then these heteroatoms are not adjacent to one another. It is preferred that the total number of S and O atoms in the heterocycle is not more than one. Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4H-carbazolyl, α-, β-, or γ-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylpyrimidinyl, phenanthridinyl, phenanthrolinyl, phenoxazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl. Also included are fused ring and spiro compounds containing, for example, the above heterocycles.

"Heteroarylmethyl," as used herein, refers to the group R—CH$_2$— where R is a heteroaryl group, as defined herein.

"Heteroarylmethyloxy," as used herein, refers to the group R—CH$_2$—O— where R is a heteroaryl group, as defined herein.

"Heteroaryloxy," as used herein, refers to the group R—O— where R is a heteroaryl group, as defined herein.

"Heteroarylmethyloxy," as used herein, refers to the group R—CH$_2$—O— where R is a heteroaryl group, as defined herein.

"Cycloalkyl," as used herein, refers to an optionally substituted, alkyl group having one or more rings in their structures having from 3 to about 20 carbon atoms (and all combinations and subcombinations of ranges and specific numbers of carbon atoms therein), with from 3 to about 10 carbon atoms being preferred. Multi-ring structures may be bridged or fused ring structures. Groups include, but are not limited to, cyclopropyl, cyclobutyl, cyclopentyl, cyclohexyl, cyclooctyl, 2-[4-isopropyl-1-methyl-7-oxa-bicyclo[2.2.1]heptanyl], 2-[1,2,3,4-tetrahydro-naphthalenyl], and adamantyl.

"Cycloalkylmethyl," as used herein, refers to the group R—CH$_2$— where R is a cycloalkyl group, as defined herein.

"Cycloalkenyl," as used herein, refers to an optionally substituted, alkene group having one or more rings in their structures having from 3 to about 20 carbon atoms (and all combinations and subcombinations of ranges and specific numbers of carbon atoms therein), with from 3 to about 10 carbon atoms being preferred. Multi-ring structures may be bridged or fused ring structures. Groups include, but are not limited to, cyclopropenyl, cyclobutenyl, cyclopentenyl, cyclohexenyl, cyclooctenyl.

"Cycloalkenylmethyl," as used herein, refers to the group R—CH$_2$— where R is a cycloalkenyl group, as defined herein.

"Sulfoxide," as used herein, refers to a compound or moiety containing the group —S(=O)—.

"Sulfonamido," as used herein, refers to a moiety containing the group —S(O)$_2$—NH—.

"Sulfonyl," as used herein, refers to a moiety containing the group —S(O)$_2$—.

"Halo" or "halogen," as used herein, refers to chloro, bromo, fluoro, and iodo.

In one embodiment, the present invention is directed to compounds of formula I:

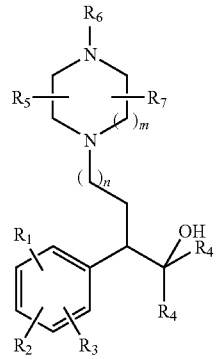

I or a pharmaceutically acceptable salt thereof;
wherein:
$R^1$, $R^2$ and $R^3$ are, independently, H, OH, alkyl, alkoxy, alkanoyloxy, CF$_3$, halo, or methylenedioxy;
$R^4$, taken together with the carbon atom to which they are attached, form a cycloalkyl ring of 4 to 8 carbon atoms;
$R^5$, $R^6$, and $R^7$ are, independently, H or (C$_1$-C$_4$)alkyl, provided that at least one of $R^5$, $R^6$, and $R^7$ is other than H;

or $R^5$ and $R^6$, together with the nitrogen atom to which $R^6$ is attached, form a heterocyclic ring;
m is 1, 2, or 3; and
n is 0, 1, 2, or 3.

In certain preferred embodiments, $R^1$, $R^2$ and $R^3$ are, independently, H, OH, alkyl (especially methyl, ethyl, butyl, and propyl), and alkoxy (especially methoxy and ethoxy). Preferably, $R_1$ is halogen, methoxy, or trifluoromethyl. Preferably, $R_2$ is hydrogen, halogen, methoxy, or trifluoromethyl. Preferably, $R_3$ is hydrogen.

In certain preferred embodiments, the $R^4$ values together form a cycloalkyl of 4 to 7 carbon atoms (especially cyclobutyl, cyclopentyl, and cyclohexyl);

In certain preferred embodiments, $R^5$, $R^6$, and $R^7$ are, independently, H or (C$_1$-C$_4$)alkyl (especially methyl and ethyl). Preferably, $R_5$ and $R_7$ are, independently, hydrogen or methyl. Preferably, $R_6$ is hydrogen or methyl.

In certain preferred embodiments, $R^5$ and $R^6$, together with the nitrogen atom to which $R^6$ is attached, form a heterocyclic ring, e.g. mono- or bicyclic of 5 to 10 ring members, saturated, partially saturated or unsaturated; preferably monocyclic of 5-7 ring atoms.

In certain preferred embodiments, m is 1. In certain preferred embodiments, m is 2. In certain preferred embodiments, m is 3.

In certain preferred embodiments, n is 0 or 1. In certain preferred embodiments, n is 2. In certain preferred embodiments, n is 3.

Preferred compounds of formula I include:
1-[1-(3-chlorophenyl)-2-piperazin-1-ylethyl]cyclohexanol;
1-{1-(3-chlorophenyl)-2-[(3R,5S)-3,5-dimethylpiperazin-1-yl]ethyl}cyclohexanol;
1-[1-(3-bromophenyl)-2-piperazin-1-ylethyl]cyclohexanol;
1-{1-(3-chlorophenyl)-2-[(3S)-3-methylpiperazin-1-yl]ethyl}cyclohexanol;
1-{1-(3-chlorophenyl)-2-[(3R)-3-methylpiperazin-1-yl]ethyl}cyclohexanol;
1-[1-(3,4-dichlorophenyl)-2-piperazin-1-ylethyl]cyclohexanol;
1-[1-(3-bromophenyl)-2-piperazin-1-ylethyl]cycloheptanol;
1-[1-(3-chlorophenyl)-2-piperazin-1-ylethyl]cycloheptanol;
1-[1-(3-fluorophenyl)-2-piperazin-1-ylethyl]cyclohexanol;
1-[1-(3-chlorophenyl)-2-piperazin-1-ylethyl]cyclopentanol;
1-[1-(4-fluorophenyl)-2-piperazin-1-ylethyl]cyclohexanol;
1-[1-(4-bromophenyl)-2-piperazin-1-ylethyl]cyclobutanol;
1-[1-(3-bromo-4-methoxyphenyl)-2-piperazin-1-ylethyl]cyclopentanol;
1-{2-piperazin-1-yl-1-[3-(trifluoromethyl)phenyl]ethyl}cyclobutanol;
1-{2-(4-methylpiperazin-1-yl)-1-[3-(trifluoromethyl)phenyl]ethyl}cyclobutanol;
1-[1-(3-bromophenyl)-2-piperazin-1-ylethyl]cyclopentanol;
1-[1-(4-bromophenyl)-2-piperazin-1-ylethyl]cyclohexanol;
1-[1-(4-chlorophenyl)-2-piperazin-1-ylethyl]cyclobutanol;
1-[1-(4-fluorophenyl)-2-piperazin-1-ylethyl]cyclobutanol;
1-[1-(4-bromophenyl)-2-piperazin-1-ylethyl]cyclobutanol;
1-[1-(4-bromophenyl)-2-(4-methylpiperazin-1-yl)ethyl]cyclobutanol;
1-[1-(3-fluorophenyl)-2-piperazin-1-ylethyl]cyclobutanol;
1-[1-(3-chlorophenyl)-2-piperazin-1-ylethyl]cyclobutanol;
1-[1-(3-chlorophenyl)-2-(4-methylpiperazin-1-yl)ethyl]cyclobutanol;
1-[1-(2-fluorophenyl)-2-piperazin-1-ylethyl]cyclohexanol;
1-[1-(4-chlorophenyl)-2-piperazin-1-ylethyl]cyclohexanol;
1-[1-(3-bromophenyl)-2-piperazin-1-ylethyl]cyclobutanol;
1-[1-(2-fluorophenyl)-2-piperazin-1-ylethyl]cyclobutanol;

1-[1-(3-fluorophenyl)-2-(4-methylpiperazin-1-yl)ethyl]cyclobutanol;
1-[1-(4-chlorophenyl)-2-(4-methylpiperazin-1-yl)ethyl]cyclobutanol;
1-[1-(2-fluorophenyl)-2-(4-methylpiperazin-1-yl)ethyl]cyclobutanol;
1-[1-(4-fluorophenyl)-2-(4-methylpiperazin-1-yl)ethyl]cyclobutanol;
1-[1-(2-bromophenyl)-2-piperazin-1-ylethyl]cyclohexanol;
1-[(1S)-1-(3-chlorophenyl)-2-piperazin-1-ylethyl]cyclohexanol;
1-[(1R)-1-(3-chlorophenyl)-2-piperazin-1-ylethyl]cyclohexanol;
1-[1-(3-chlorophenyl)-2-piperazin-1-ylethyl]cyclooctanol;
1-[1-(3-bromophenyl)-2-piperazin-1-ylethyl]cyclooctanol;
1-[1-(3-bromo-4-methoxyphenyl)-2-piperazin-1-ylethyl]cyclooctanol;
1-[1-(3-chlorophenyl)-2-(4-methylpiperazin-1-yl)ethyl]cyclooctanol;
1-[1-(3-bromophenyl)-2-(4-methylpiperazin-1-yl)ethyl]cyclooctanol; and
pharmaceutically acceptable salts thereof.

Preferably, the pharmaceutically acceptable salt is the dihydrochloride salt.

Some of the compounds of the present invention may contain chiral centers and such compounds may exist in the form of stereoisomers (i.e. enantiomers). The present invention includes all such stereoisomers and any mixtures thereof including racemic mixtures. Racemic mixtures of the stereoisomers as well as the substantially pure stereoisomers are within the scope of the invention. The term "substantially pure," as used herein, refers to at least about 90 mole %, more preferably at least about 95 mole %, and most preferably at least about 98 mole % of the desired stereoisomer is present relative to other possible stereoisomers. Preferred enantiomers may be isolated from racemic mixtures by any method known to those skilled in the art, including high performance liquid chromatography (HPLC) and the formation and crystallization of chiral salts or prepared by methods described herein. See, for example, Jacques, et al., *Enantiomers, Racemates and Resolutions* (Wiley Interscience, New York, 1981); Wilen, S. H., et al., *Tetrahedron*, 33:2725 (1977); Eliel, E. L. *Stereochemistry of Carbon Compounds*, (McGraw-Hill, N.Y., 1962); Wilen, S. H. *Tables of Resolving Agents and Optical Resolutions*, p. 268 (E. L. Eliel, Ed., University of Notre Dame Press, Notre Dame, Ind. 1972).

The present invention includes prodrugs of the compounds of formula I. "Prodrug," as used herein, means a compound which is convertible in vivo by metabolic means (e.g. by hydrolysis) to a compound of formula I. Various forms of prodrugs are known in the art, for example, as discussed in Bundgaard, (ed.), *Design of Prodrugs*, Elsevier (1985); Widder, et al. (ed.), *Methods in Enzymology*, vol. 4, Academic Press (1985); Krogsgaard-Larsen, et al., (ed). "Design and Application of Prodrugs," *Textbook of Drug Design and Development*, Chapter 5, 113-191 (1991), Bundgaard, et al., *Journal of Drug Deliver Reviews*, 1992, 8:1-38, Bundgaard, *J. of Pharmaceutical Sciences*, 1988, 77:285 et seq.; and Higuchi and Stella (eds.) *Prodrugs as Novel Drug Delivery Systems*, American Chemical Society (1975).

Further, the compounds of formula I may exist in unsolvated as well as in solvated forms with pharmaceutically acceptable solvents such as water, ethanol, and the like. In general, the solvated forms are considered equivalent to the unsolvated forms for the purpose of the present invention.

The compounds of the present invention may be prepared in a number of ways well known to those skilled in the art. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Protecting groups that may be employed in accordance with the present invention may be described in Greene, T. W. and Wuts, P. G. M., *Protective Groups in Organic Synthesis* 2d. Ed., Wiley & Sons, 1991.

Compounds of the present invention are suitably prepared in accordance with the following general description and specific examples. Variables used are as defined for Formula I, unless otherwise noted. The reagents used in the preparation of the compounds of this invention can be either commercially obtained or can be prepared by standard procedures described in the literature. The reagents used in the preparation of the compounds of this invention can be either commercially obtained or can be prepared by standard procedures described in the literature. In accordance with this invention, compounds of formula I are produced by the following reaction schemes (Scheme 1-2).

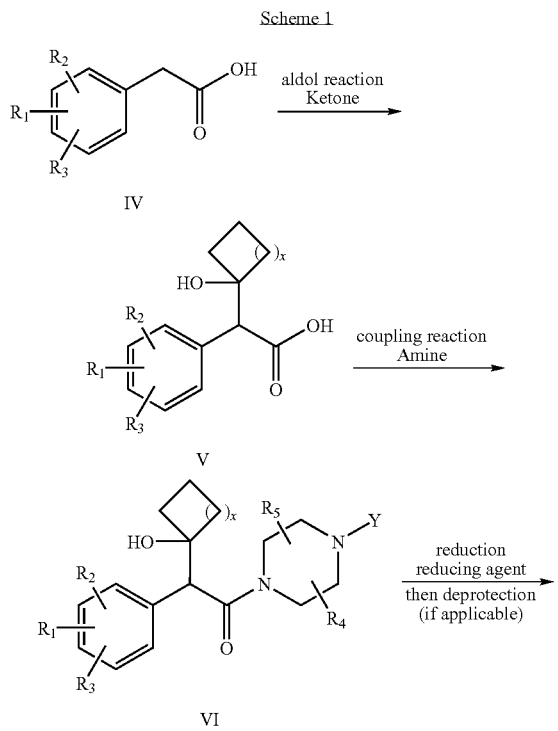

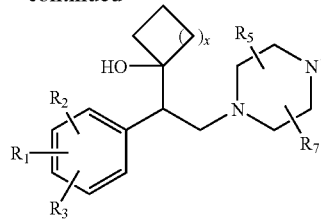

I where
Y = H, R$_6$, or P.
X = 1, 2, 3, 4, or 5
P = an amine protecting group, preferably but not limited to tert-butoxycarbonyl.

Compounds of formula I can be prepared from compounds of formula VI via reduction followed by deprotection, where Y═P; otherwise the deprotection step is omitted. Where P═tert-butoxycarbonyl, any conventional method for the deprotection of a carbamate can be utilized for this conversion. In accordance with the preferred embodiment of this invention, deprotection is carried out using a protic acid, i.e., hydrochloric acid. Reduction is performed using any conventional method of reducing an amide to an amine. In accordance with the preferred embodiment of this invention, the compounds of formula VI are treated with a solution of borane in tetrahydrofuran and heated at 70-80° C.

Compounds of formula VI can be prepared via the coupling of compounds of formula V with an appropriately substituted secondary or primary amine. The reaction is carried out by any conventional method for the activation of a carboxylic acid to form an amide. In the preferred embodiment of this invention, the carboxylic acid is treated with benzotriazol-1-yloxytris(dimethylamino)phosphonium hexafluoro phosphate in the presence of an appropriately substituted secondary or primary amine and triethylamine.

Compounds of formula V are prepared by reacting an appropriately substituted ketone with a phenylacetic acid of formula IV via an aldol reaction. The phenylacetic acids of formula IV can be either commercially obtained or prepared by standard procedures described in the literature. Compounds of formula IV represent an organic acid having an alpha carbon atom, so reaction with a ketone occurs at the alpha carbon atom of this carboxylic acid. This reaction is carried out by any conventional means of reacting the alpha carbon atom of a carboxylic acid with a ketone. Generally, in these aldol reactions, a ketone is reacted with the dianion of the acetic acid. The anion can be generated by using a strong organic base such as lithium diisopropylamide, as well as other organic lithium bases. This reaction is performed in low boiling point solvents such as tetrahydrofuran at low temperatures from −80° C. to about −50° C. being preferred.

Scheme 2

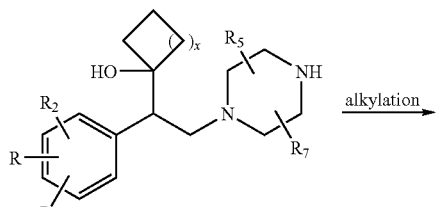

I

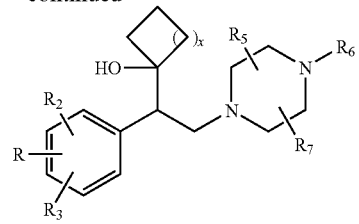

VII

If it is desired to produce compounds of formula VII, they can be formed from compounds of formula I via an alkylation with an alkyl halide or via a reductive amination with an aldehyde or ketone. Any conventional method of alkylating a secondary amine with an alkyl halide can be utilized. In addition, any conventional method of performing a reductive amination can be utilized. In accordance with the preferred embodiment of this invention, when it is desired to form compounds of formula VII where R$_3$═methyl, a mixture of the amine and formaldehyde in formic acid is heated at 60° C.-80° C. If is desired to form compounds of formula VII where R$_3$═lower alkyl other than methyl, a mixture of the amine and an appropriately substituted aldehyde or ketone in methylene chloride is treated with trisacetoxyborohydride.

The compounds of formula I have an asymmetric carbon atom. In accordance with this invention the preferred stereo-configuration is S. If it is desired to produce the R or the S isomer of the compounds of formula I, these compounds can be isolated as the desired isomer by any conventional method. Among the preferred means is to separate the isomers of either the amide of formula V or the amine of formula VI or formula VII via Supercritical Fluid Chromatography.

The separation of R and S isomers can also be achieved by forming a lower alkyl ester of phenylacetic acids of formula IV. Any conventional method for the formation of an ester from a carboxylic acid can be utilized. Separation is performed using an enzymatic ester hydrolysis of any lower alkyl esters corresponding to the compound of formula IV (See, for example, Ahmar, M.; Girard, C.; Bloch, R. *Tetrahedron Lett.*, 1989, 7053), which results in the formation of corresponding chiral acid and chiral ester. The ester and the acid can be separated by any conventional method of separating an acid from an ester.

In other embodiments, the invention is directed to pharmaceutical compositions, comprising:
a. at least compound of formula I or pharmaceutically acceptable salt thereof; and
b. at least one pharmaceutically acceptable carrier.

Generally, the compound of formula I or a pharmaceutically acceptable salt thereof will be present at a level of from about 0.1%, by weight, to about 90% by weight, based on the total weight of the pharmaceutical composition, based on the total weight of the pharmaceutical composition. Preferably, the compound of formula I or a pharmaceutically acceptable salt thereof will be present at a level of at least about 1%, by weight, based on the total weight of the pharmaceutical composition. More preferably, the compound of formula I or a pharmaceutically acceptable salt thereof will be present at a level of at least about 5%, by weight, based on the total weight of the pharmaceutical composition. Even more preferably, the norepinephrine reuptake inhibitor or a pharmaceutically acceptable salt thereof will be present at a level of at least about 10%, by weight, based on the total weight of the pharmaceutical composition. Yet even more preferably, the compound of formula I or a pharmaceutically acceptable salt thereof will be present at a level of at least about 25%, by weight, based on the total weight of the pharmaceutical composition.

Such compositions are prepared in accordance with acceptable pharmaceutical procedures, such as described in *Remington's Pharmaceutical Sciences,* 17th edition, ed. Alfonoso R. Gennaro, Mack Publishing Company, Easton, Pa. (1985). Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances that may also act as flavoring agents, lubricants, solubilizers, suspending agents, fillers, glidants, compression aids, binders or tablet-disintegrating agents or an encapsulating material. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups, and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions, which are sterile solutions or suspensions, can be administered by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

In another embodiment of the present invention, the compounds useful in the present invention may be administered to a mammal with one or more other pharmaceutical active agents such as those agents being used to treat any other medical condition present in the mammal. Examples of such pharmaceutical active agents include pain relieving agents, anti-angiogenic agents, anti-neoplastic agents, anti-diabetic agents, anti-infective agents, or gastrointestinal agents, or combinations thereof.

The one or more other pharmaceutical active agents may be administered in a therapeutically effective amount simultaneously (such as individually at the same time, or together in a pharmaceutical composition), and/or successively with one or more compounds of the present invention.

The term "combination therapy" refers to the administration of two or more therapeutic agents or compounds to treat a therapeutic condition or disorder described in the present disclosure, for example hot flush, sweating, thermoregulatory-related condition or disorder, or other. Such administration includes use of each type of therapeutic agent in a concurrent manner. In either case, the treatment regimen will provide beneficial effects of the drug combination in treating the conditions or disorders described herein.

The route of administration may be any route, which effectively transports the active compound of formula I to the appropriate or desired site of action, such as oral, nasal, pulmonary, transdermal, such as passive or iontophoretic delivery, or parenteral, e.g. rectal, depot, subcutaneous, intravenous, intraurethral, intramuscular, intranasal, ophthalmic solution or an ointment. Furthermore, the administration of compound of formula I with other active ingredients may be concurrent or simultaneous.

It is believed that the present invention described presents a substantial breakthrough in the field of treatment, alleviation, inhibition, and/or prevention of conditions ameliorated by monoamine reuptake including, inter alia, vasomotor symptoms (VMS), sexual dysfunction, gastrointestinal and genitourinary disorders, chronic fatigue syndrome, fibromyalgia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

Accordingly, in one embodiment, the present invention is directed to methods for treating or preventing a condition ameliorated by monoamine reuptake in a subject in need thereof, comprising the step of:

administering to said subject an effective amount of a compound of formula I or pharmaceutically acceptable salt thereof.

The conditions ameliorated by monoamine reuptake include those selected from the group consisting of vasomotor symptoms, sexual dysfunction, gastrointestinal and genitourinary disorders, chronic fatigue syndrome, fibromyalgia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

"Vasomotor symptoms," "vasomotor instability symptoms" and "vasomotor disturbances" include, but are not limited to, hot flushes (flashes), insomnia, sleep disturbances, mood disorders, irritability, excessive perspiration, night sweats, fatigue, and the like, caused by, inter alia, thermoregulatory dysfunction.

The term "hot flush" is an art-recognized term that refers to an episodic disturbance in body temperature typically consisting of a sudden skin flushing, usually accompanied by perspiration in a subject.

The term "sexual dysfunction" includes, but is not limited to, condition relating to desire and/or arousal.

As used herein, "gastrointestinal and genitourinary disorders" includes irritable bowel syndrome, symptomatic GERD, hypersensitive esophagus, nonulcer dyspepsia, noncardiac chest pain, biliary dyskinesia, sphincter of Oddi dysfunction, incontinence (i.e., urge incontinence, stress incontinence, genuine stress incontinence, and mixed incontinence)(including the involuntary voiding of feces or urine, and dribbling or leakage or feces or urine which may be due to one or more causes including but not limited to pathology altering sphincter control, loss of cognitive function, overdistention of the bladder, hyperreflexia and/or involuntary urethral relaxation, weakness of the muscles associated with the bladder or neurologic abnormalities), interstitial cystitis (irritable bladder), and chronic pelvic pain (including, but not limited to vulvodynia, prostatodynia, and proctalgia).

As used herein, "chronic fatigue syndrome" (CFS) is a condition characterized by physiological symptoms selected from weakness, muscle aches and pains, excessive sleep, malaise, fever, sore throat, tender lymph nodes, impaired memory and/or mental concentration, insomnia, disordered sleep, localized tenderness, diffuse pain and fatigue, and combinations thereof.

As used herein, "fibromyalgia syndrome" (FMS) includes FMS and other somatoform disorders, including FMS associated with depression, somatization disorder, conversion disorder, pain disorder, hypochondriasis, body dysmorphic disorder, undifferentiated somatoform disorder, and somatoform NOS. FMS and other somatoform disorders are accompanied by physiological symptoms selected from a generalized heightened perception of sensory stimuli, abnormalities in pain perception in the form of allodynia (pain with innocuous stimulation), abnormalities in pain perception in the form of hyperalgesia (increased sensitivity to painful stimuli), and combinations thereof.

As used herein, "nervous system disorders," includes addictive disorders (including those due to alcohol, nicotine, and other psychoactive substances) and withdrawal syndrome, age-associated learning and mental disorders (including Alzheimer's disease), anorexia nervosa, bulimia nervosa, attention-deficit disorder with or without hyperactivity disorder bipolar disorder, pain (including chronic pain selected from the group consisting of lower back pain, atypical chest pain, headache such as cluster headache, migraine, herpes neuralgia, phantom limb pain, pelvic pain, myofascial face pain, abdominal pain, neck pain, central pain, dental pain, opioid resistant pain, visceral pain, surgical pain, bone injury pain, pain during labor and delivery, pain resulting from burns, post partum pain, angina pain, neuropathic pain such as peripheral neuropathy and diabetic neuropathy, post-operative pain, and pain which is co-morbid with nervous system disorders described herein), cyclothymic disorder, depression disorder (including major depressive disorder, refractory depression adolescent depression and minor depression), dysthymic disorder, generalized anxiety disorder (GAD), obesity (i.e., reducing the weight of obese or overweight patients), obsessive compulsive disorders and related spectrum disorders, oppositional defiant disorder, panic disorder, post-traumatic stress disorder, premenstrual dysphoric disorder (i.e., premenstrual syndrome and late luteal phase dysphoric disorder), psychotic disorders (including schizophrenia, schizoaffective and schizophreniform disorders), seasonal affective disorder, sleep disorders (such as narcolepsy and enuresis), social phobia (including social anxiety disorder), selective serotonin reuptake inhibition (SSRI) "poop out" syndrome (i.e., wherein a patient who fails to maintain a satisfactory response to SSRI therapy after an initial period of satisfactory response).

In one embodiment, the present invention is directed to methods for treating or preventing vasomotor symptoms in a subject in need thereof, comprising the step of:
  administering to said subject an effective amount of at least one compound of formula I or pharmaceutically acceptable salt thereof.

When estrogen levels are low or estrogen is absent, the normal levels between NE and 5-HT is altered and this altered change in neurotransmitter levels may result in changes in the sensitivity of the thermoregulatory center. The altered chemical levels may be translated in the thermoregulatory center as heat sensation and as a response, the hypothalamus may activate the descending autonomic pathways and result in heat dissipation via vasodilation and sweating (hot flush) (FIG. 1). Accordingly, the estrogen deprivation may result in altered norepinephrine activity.

Figure 2:
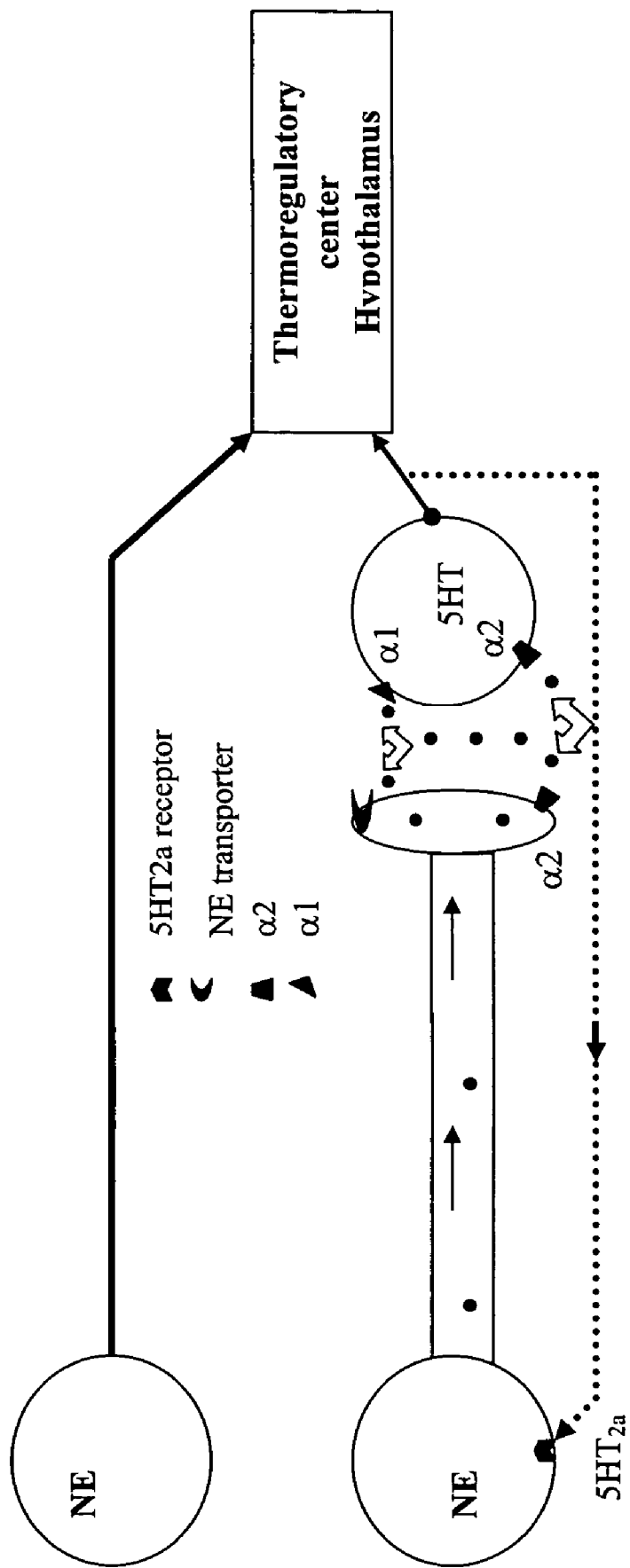
FIG. 2 is a schematic representation of the interactions of norepinephrine and serotonin and their respective receptors (5-$HT_{2a}$, $\alpha_1$ and $\alpha_2$-adrenergic).

Norepinephrine synthesized in perikarya of the brainstem is released at the nerve terminals in the hypothalamus and brainstem. In the hypothalamus, NE regulates the activity of neurons residing in the thermoregulatory center. In the brainstem, NE innervates serotoninergic neurons (5HT), and acting via adrenergic$_{\alpha 1}$ and adrenergic$_{\alpha 2}$ postsynaptic receptors, it stimulates the activity of the serotoninergic system. In response, 5-HT neurons also modulate the activity the thermoregulatory center and feedback to NE neurons. Via this feedback connection, 5-HT, acting via 5-HT$_{2a}$ receptors, inhibit the activity of NE neurons. Norepinephrine in the synaptic cleft is also taken up by NE transporter (NET) located in NE neurons. The transporter recycles NE and makes it available for multiple neurotransmission (FIG. 2).

The present invention provides a treatment for vasomotor symptoms by methods of recovering the reduced activity of norepinephrine. Norepinephrine activity in the hypothalamus or in the brainstem can be elevated by (i) blocking the activity of the NE transporter, (ii) blocking the activity of the presynaptic adrenergic$_{\alpha 2}$ receptor with an antagonist, or (iii) blocking the activity of 5-HT on NE neurons with a 5-HT$_{2a}$ antagonist.

In another embodiment, the present invention is directed to methods for treating or preventing a depression disorder in a subject in need thereof, comprising the step of:
  administering to said subject an effective amount of at least one compound of formula I or pharmaceutically acceptable salt thereof.

In yet other embodiments, the present invention is directed to methods for treating or preventing sexual dysfunction in a subject in need thereof, comprising the step of:
  administering to said subject an effective amount of at least one compound of formula I or pharmaceutically acceptable salt thereof.

In another embodiment, the present invention is directed to methods for treating or preventing gastrointestinal or genitourinary disorder, particularly stress incontinence or urge urinary incontinence, in a subject in need thereof, comprising the step of:
  administering to said subject an effective amount of a compound of formula I or pharmaceutically acceptable salt thereof.

In another embodiment, the present invention is directed to methods for treating or preventing chronic fatigue syndrome in a subject in need thereof, comprising the step of:

administering to said subject an effective amount of a compound of formula I or pharmaceutically acceptable salt thereof.

In another embodiment, the present invention is directed to methods for treating or preventing fibromyalgia syndrome in a subject in need thereof, comprising the step of:
administering to said subject an effective amount of a compound of formula I or pharmaceutically acceptable salt thereof.

In further embodiments, the present invention is directed to methods for treating or preventing pain in a subject in need thereof, comprising the step of:
administering to said subject an effective amount of at least one compound of formula I or pharmaceutically acceptable salt thereof.

The pain may be, for example, acute pain (short duration) or chronic pain (regularly reoccurring or persistent). The pain may also be centralized or peripheral.

Examples of pain that can be acute or chronic and that can be treated in accordance with the methods of the present invention include inflammatory pain, musculoskeletal pain, bony pain, lumbosacral pain, neck or upper back pain, visceral pain, somatic pain, neuropathic pain, cancer pain, pain caused by injury or surgery such as burn pain or dental pain, or headaches such as migraines or tension headaches, or combinations of these pains. One skilled in the art will recognize that these pains may overlap one another. For example, a pain caused by inflammation may also be visceral or musculoskeletal in nature.

In a preferred embodiment of the present invention the compounds useful in the present invention are administered in mammals to treat chronic pain such as neuropathic pain associated for example with damage to or pathological changes in the peripheral or central nervous systems; cancer pain; visceral pain associated with for example the abdominal, pelvic, and/or perineal regions or pancreatitis; musculoskeletal pain associated with for example the lower or upper back, spine, fibromyalgia, temporomandibular joint, or myofascial pain syndrome; bony pain associated with for example bone or joint degenerating disorders such as osteoarthritis, rheumatoid arthritis, or spinal stenosis; headaches such migraine or tension headaches; or pain associated with infections such as HIV, sickle cell anemia, autoimmune disorders, multiple sclerosis, or inflammation such as osteoarthritis or rheumatoid arthritis.

In a more preferred embodiment, the compounds useful in this invention are used to treat chronic pain that is neuropathic pain, visceral pain, musculoskeletal pain, bony pain, cancer pain or inflammatory pain or combinations thereof, in accordance with the methods described herein. Inflammatory pain can be associated with a variety of medical conditions such as osteoarthritis, rheumatoid arthritis, surgery, or injury. Neuropathic pain may be associated with for example diabetic neuropathy, peripheral neuropathy, post-herpetic neuralgia, trigeminal neuralgia, lumbar or cervical radiculopathies, fibromyalgia, glossopharyngeal neuralgia, reflex sympathetic dystrophy, casualgia, thalamic syndrome, nerve root avulsion, or nerve damage cause by injury resulting in peripheral and/or central sensitization such as phantom limb pain, reflex sympathetic dystrophy or postthoracotomy pain, cancer, chemical injury, toxins, nutritional deficiencies, or viral or bacterial infections such as shingles or HIV, or combinations thereof. The methods of use for compounds of this invention further include treatments in which the neuropathic pain is a condition secondary to metastatic infiltration, adiposis dolorosa, burns, or central pain conditions related to thalamic conditions.

As mentioned previously, the methods of the present invention may be used to treat pain that is somatic and/or visceral in nature. For example, somatic pain that can be treated in accordance with the methods of the present invention include pains associated with structural or soft tissue injury experienced during surgery, dental procedures, burns, or traumatic body injuries. Examples of visceral pain that can be treated in accordance with the methods of the present invention include those types of pain associated with or resulting from maladies of the internal organs such as ulcerative colitis, irritable bowel syndrome, irritable bladder, Crohn's disease, rheumatologic (arthralgias), tumors, gastritis, pancreatitis, infections of the organs, or biliary tract disorders, or combinations thereof. One skilled in the art will also recognize that the pain treated according to the methods of the present invention may also be related to conditions of hyperalgesia, allodynia, or both. Additionally, the chronic pain may be with or without peripheral or central sensitization.

The compounds useful in this invention may also be used to treat acute and/or chronic pains associated with female conditions, which may also be referred to as female-specific pain. Such groups of pain include those that are encountered solely or predominately by females, including pain associated with menstruation, ovulation, pregnancy or childbirth, miscarriage, ectopic pregnancy, retrograde menstruation, rupture of a follicular or corpus luteum cyst, irritation of the pelvic viscera, uterine fibroids, adenomyosis, endometriosis, infection and inflammation, pelvic organ ischemia, obstruction, intra-abdominal adhesions, anatomic distortion of the pelvic viscera, ovarian abscess, loss of pelvic support, tumors, pelvic congestion or referred pain from non-gynecological causes.

EXAMPLES

The present invention is further defined in the following Examples, in which all parts and percentages are by weight and degrees are Celsius, unless otherwise stated. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various usages and conditions.

Reference Example 1-a

Aldol Reaction: Preparation of Acid Intermediates

A solution of diisopropylamine (7.87 mL, 56.2 mmol) in dry tetrahydrofuran (50 mL) under nitrogen was cooled to −78° C. and treated dropwise with a solution of n-butyllithium (2.5 M in hexanes, 22 mL, 55.0 mmol). The resulting solution was warmed to 0° C. and stirred for 15 min. The solution was re-cooled to −78° C. and treated, via cannula, with a solution of 3-chlorophenylacetic acid (4.0 g, 23.4 mmol) in tetrahydrofuran (20 mL). The reaction was then allowed to warm to 25° C. where it was stirred for 45 minutes and was then re-cooled to −78° C. A solution of cyclohexanone (3.65 mL, 35.3 mL) in tetrahydrofuran (10 mL) was then added via cannula, and the resulting mixture was stirred at −78° C. for 1.5 h. The reaction was then quenched by the addition of a saturated aqueous solution of ammonium chloride, and the tetrahydrofuran was removed in vacuo. The resulting residue was dissolved in a 2N aqueous solution of sodium hydroxide (30 mL) and washed with ethyl acetate (1×30 mL). The aqueous layer was then acidified to pH=1 with the addition of a 2 N aqueous solution of hydrochloric acid. The product was extracted with ethyl acetate (3×30 mL), and combined organic extracts were dried over magnesium sulfate and concentrated in vacuo to yield 6.05 g (96%) of pure (3-chlorophenyl)(1-hydroxycyclohexyl)acetic acid as a white solid. HRMS: calcd for $C_{14}H_{17}ClO_3$, 268.0866; found (ESI_FT), 291.0748.

b) In an analogous manner, (3-bromophenyl)(1-hydroxycyclohexyl)acetic acid was prepared from 3-bromophenylacetic acid and cyclohexanone. HRMS: calcd for $C_{14}H_{17}BrO_3$, 312.0361; found (ESI_FT), 350.99924.

c) In an analogous manner, 3,4-dichloro-alpha-(1-hydroxycyclohexyl)benzeneacetic acid was prepared from 3,4-dichlorophenylacetic acid and cyclohexanone. MS (ESI) m/z 301/303/305 ([M−H]⁻); Anal. Calcd for $C_{14}H_{16}Cl_2O_3$: C, 55.46; H, 5.32; N, 0.00. Found: C, 55.42; H, 5.30; N, 0.00.

d) In an analogous manner, (4-bromophenyl)(1-hydroxycyclohexyl)acetic acid was prepared from 4-bromophenylacetic acid and cyclohexanone. MS (ESI) m/z 313/315 ([M+H]⁺); Anal. Calcd for $C_{14}H_{17}BrO_3$: C, 53.69; H, 5.47; N, 0.00. Found: C, 53.87; H, 5.42; N, 0.00.

e) In an analogous manner, (3-bromophenyl)(1-hydroxycyclobutyl)acetic acid was prepared from 3-bromophenylacetic acid and cyclobutanone. HRMS: calcd for $C_{12}H_{13}BrO_3$, 284.0048; found (ESI_FT), 306.99337.

f) In an analogous manner, (3-bromo-4-methoxyphenyl)(1-hydroxycyclohexyl)acetic acid was prepared from 3-bromo-4-methoxyphenylacetic acid and cyclohexanone. MS (ESI) m/z 341/343 ([M−H]⁻; HRMS: calcd for $C_{15}H_{19}BrO_4$, 342.0467; found (ESI_FT), 341.03897.

g) In an analogous manner, (1-hydroxycyclohexyl)[3-(trifluoromethyl)phenyl]acetic acid was prepared from 3-trifluoromethylphenylacetic acid and cyclohexanone. MS (ESI) m/z 301 ([M−H]⁻); HRMS: calcd for $C_{15}H_{17}F_3O_3$, 302.1130; found (ESI_FT), 325.1024.

h) In an analogous manner, (3,4-dichlorophenyl)(1-hydroxycyclobutyl)acetic acid was prepared from 3,4-dichlorophenylacetic acid and cyclobutanone. HRMS: calcd for $C_{12}H_{12}Cl_2O_3$, 274.0163; found (ESI_FT), 273.00881.

i) In an analogous manner, (3-bromophenyl)(1-hydroxycycloheptyl)acetic acid was prepared from 3-bromophenylacetic acid and cycloheptanone. MS m/z 325/327 ([M−H]⁻).

j) In an analogous manner, (3-chlorophenyl)(1-hydroxycycloheptyl)acetic acid was prepared from 3-chlorophenylacetic acid and cycloheptanone. MS (ESI) m/z 281/283 ([M−H]⁻).

k) In an analogous manner, (3-fluorophenyl)(1-hydroxycyclohexyl)acetic acid was prepared from 3-fluorophenylacetic acid and cyclohexanone. HRMS: calcd for $C_{14}H_{17}FO_3$, 252.1162; found (ESI), 251.1083.

l) In an analogous manner, (4-fluorophenyl)(1-hydroxycyclohexyl)acetic acid was prepared from 4-fluorophenylacetic acid and cyclohexanone. HRMS: calcd for $C_{14}H_{17}FO_3$, 252.1162; found (ESI), 251.1077.

m) In an analogous manner, (4-bromophenyl)(1-hydroxycyclobutyl)acetic acid was prepared from 4-bromophenylacetic acid and cyclobutanone.

n) In an analogous manner, (3-bromo-4-methoxyphenyl)(1-hydroxycyclopentyl)acetic acid was prepared from 3-bromo-4-methoxyphenylacetic acid and cyclopentanone. HRMS: calcd for $C_{14}H_{17}BrO_4$, 328.0310; found (ESI_FT), 351.02036.

o) In an analogous manner, (1-hydroxycyclobutyl)[3-(trifluoromethyl)phenyl]acetic acid was prepared from 3-trifluoromethylphenylacetic acid and cyclobutanone. MS (ES) m/z 273.1 ([M−H]⁻); HRMS: calcd for $C_{13}H_{13}F_3O_3$, 274.0817; found (ESI), 273.0736.

p) In an analogous manner, (3-bromophenyl)(1-hydroxycyclopentyl)acetic acid was prepared from 3-bromophenylacetic acid and cyclopentanone. MS (ESI) m/z 297/299 ([M+H]⁺); HRMS: calcd for $C_{13}H_{15}BrO_3$, 298.0205; found (ESI_FT), 321.00963.

q) In an analogous manner, (4-chlorophenyl)(1-hydroxycyclobutyl)acetic acid was prepared from 4-chlorophenylacetic acid and cyclobutanone. HRMS: calcd for $C_{12}H_{13}ClO_3$, 240.0553; found (ESI), 239.0486.

r) In an analogous manner, (4-fluorophenyl)(1-hydroxycyclobutyl)acetic acid was prepared from 4-fluorophenylacetic acid and cyclobutanone. HRMS: calcd for $C_{12}H_{13}FO_3$, 224.0849; found (ESI), 223.0777.

s) In an analogous manner, (2-bromophenyl)(1-hydroxycyclohexyl)acetic acid was prepared from 2-bromophenylacetic acid and cyclohexanone. MS (ESI) m/z 311/313 ([M−H]⁻).

t) In an analogous manner, (3-fluorophenyl)(1-hydroxycyclobutyl)acetic acid was prepared from 3-fluorophenylacetic acid and cyclobutanone. HRMS: calcd for $C_{12}H_{13}FO_3$, 224.0849; found (ESI), 223.0778.

u) In an analogous manner, (3-chlorophenyl)(1-hydroxycyclobutyl)acetic acid was prepared from 3-chlorophenylacetic acid and cyclobutanone. MS (ESI) m/z 239/241 ([M−H]⁻); HRMS: calcd for $C_{12}H_{13}ClO_3$, 240.0553; found (ESI), 239.0472; Anal. Calcd for $C_{12}H_{13}ClO_3$: C, 59.88; H, 5.44; N, 0.00. Found: C, v) 59.71; H, 5.28; N, 0.00.

w) In an analogous manner, (2-fluorophenyl)(1-hydroxycyclohexyl)acetic acid was prepared from 2-fluorophenylacetic acid and cyclohexanone. MS (ES) m/z 251.1 ([M−H]⁻); HRMS: calcd for $C_{14}H_{17}FO_3$, 252.1162; found (ESI), 251.107.

x) In an analogous manner, (4-chlorophenyl)(1-hydroxycyclohexyl)acetic acid was prepared from 4-chlorophenylacetic acid and cyclohexanone. HRMS: calcd for $C_{14}H_{17}ClO_3$, 268.0866; found (ESI), 267.0792.

y) In an analogous manner, (2-fluorophenyl)(1-hydroxycyclobutyl)acetic acid was prepared from 2-fluorophenylacetic acid and cyclobutanone. MS (ES) m/z 223.1 ([M−H]⁻); HRMS: calcd for $C_{12}H_{13}FO_3$, 224.0849; found (ESI), 223.0763.

z) In an analogous manner, (3-chlorophenyl)(1-hydroxycyclopentyl])acetic acid was prepared from 3-chlorophenylacetic acid and cyclopentanone.

Example 1

1-[1-(3-chlorophenyl)-2-piperazin-1-ylethyl]cyclohexanol dihydrochloride

Step 1: A solution of (3-chlorophenyl)(1-hydroxycyclohexyl)acetic acid (Reference Example 1-a) (5.4 g, 20.1 mmol), benzotriazol-1-yloxytris(dimethylamino)phosphonium hexafluorophosphate (14.22 g, 32.15 mmol), and tert-butyl 1-piperazinecarboxylate (5.99 g, 32.15 mmol) in methylene chloride (20 mL) was treated with triethylamine (8.4 mL, 60.3 mmol). The reaction was stirred at 25° C. for 16 h, after which time the solvent was removed in vacuo and the product was purified via Biotage Horizon (FLASH 40 M, silica, gradient from 0% EtOAc/hexane to 30% EtOAc/hexane) to yield 7.10 g (81%) tert-butyl 4-[(3-chlorophenyl)(1- hydroxycyclohexyl)acetyl]piperazine-1-carboxylate as a white foam. HRMS: calcd for $C_{23}H_{33}ClN_2O_4$, 436.2129; found (ESI_FT), 437.21996.

Step 2: A solution of 4-[(3-chlorophenyl)(1-hydroxycyclohexyl)acetyl]piperazine-1-carboxylate (200 mg, 0.46 mmol) in dry tetrahydrofuran (3 mL) under nitrogen was treated dropwise with a solution of borane (1.0 M in tetrahydrofuran, 1.60 mL, 1.60 mmol). The resulting solution was heated at 70° C. for 2 h, after which time the reaction was cooled in an ice bath and was treated dropwise with a 2N aqueous solution of hydrochloric acid (1 mL). The reaction was again heated at 70° C. for 1 h, and was then cooled and treated with methanol (1 mL). After the solvent was removed in vacuo, the resulting residue was dissolved in water (5 mL) and was washed with ethyl acetate (1×4 mL). The aqueous layer was basified with the addition of a 2 N aqueous solution of sodium hydroxide until the pH=10. The product was extracted with ethyl acetate (4×5 mL) and the combined organic extracts were dried over magnesium sulfate and concentrated in vacuo to yield 146 mg (99%) 1-[1-(3-chlorophenyl)-2-piperazin-1-ylethyl]cyclohexanol as a colorless oil. HRMS: calcd for $C_{18}H_{27}ClN_2O$, 322.1812; found (ESI_FT), 323.18977. 1-[1-(3-Chlorophenyl)-2-piperazin-1-ylethyl]cyclohexanol (146 mg) was dissolved in methanol (0.5 mL) and treated with a saturated methanolic solution of hydrochloric acid (0.5 mL) followed by diethyl ether. After crystallizing in the refrigerator for 16 h, the resulting solid was filtered, washed with diethyl ether and dried in vacuo to yield 110 mg (60%) 1-[1-(3-chlorophenyl)-2-piperazin-1-ylethyl]cyclohexanol dihydrochloride as a white solid. MS (ESI) m/z 323/325 ([M+H]$^+$); HRMS: calcd for $C_{18}H_{27}ClN_2O.2.00$ HCl, 394.1345; found (ESI_FT), 323.18831.

Example 2

1-{1-(3-chlorophenyl)-2-[(3R,5S)-3,5-dimethylpiperazin-1-yl]ethyl}cyclohexanol dihydrochloride In an analogous manner to Example 1, step 1 1-{1-(3-chlorophenyl)-2-[(3R,5S)-3,5-dimethylpiperazin-1-yl]-2-oxoethyl}cyclohexanol was prepared from (3-chlorophenyl)(1-hydroxycyclohexyl)acetic acid (Reference Example 1-a) and 2,6-dimethylpiperazine.

In an analogous manner to Example 1, step 2 1-{1-(3-chlorophenyl)-2-[(3R,5S)-3,5-dimethylpiperazin-1-yl]ethyl}cyclohexanol dihydrochloride was prepared from 1-{1-(3-chlorophenyl)-2-[(3R,5S)-3,5-dimethylpiperazin-1-yl]-2-oxoethyl}cyclohexanol. MS (ESI) m/z 351/353 ([M+H]$^+$); HRMS: calcd for $C_{20}H_{31}ClN_2O$, 351.2203; found (ESI), 351.2192.

Example 3

1-[1-(3-bromophenyl)-2-piperazin-1-ylethyl]cyclohexanol dihydrochloride

In an analogous manner to Example 1, step 1 tert-butyl 4-[(3-bromophenyl)(1-hydroxycyclohexyl)acetyl]piperazine-1-carboxylate was prepared from (3-bromophenyl)(1-hydroxycyclohexyl)acetic acid (Reference Example 1-b) and tert-butyl 1-piperazinecarboxylate. HRMS: calcd for $C_{23}H_{33}BrN_2O_4$, 480.1624; found (ESI_FT), 481.16857.

In an analogous manner to Example 1, step 2 1-[1-(3-bromophenyl)-2-piperazin-1-ylethyl]cyclohexanol dihydrochloride was prepared from tert-butyl 4-[(3-bromophenyl)(1-hydroxycyclohexyl)acetyl]piperazine-1-carboxylate. HRMS: calcd for $C_{18}H_{27}BrN_2O.2.00$ HCl, 438.0840; found (ESI_FT), 367.13874.

Example 4

1-{1-(3-chlorophenyl)-2-[(3S)-3-methylpiperazin-1-yl]ethyl}cyclohexanol dihydrochloride In an analogous manner to Example 1, step 1 1-{1-(3-chlorophenyl)-2-[(3S)-3-methylpiperazin-1-yl]-2-oxoethyl}cyclohexanol was prepared from (3-chlorophenyl)(1-hydroxycyclohexyl)acetic acid (Reference Example 1-a) and (S)-(+)-2-methylpiperazine.

In an analogous manner to Example 1, step 2 1-{1-(3-chlorophenyl)-2-[(3S)-3-methylpiperazin-1-yl]ethyl}cyclohexanol dihydrochloride was prepared from 1-{1-(3-chlorophenyl)-2-[(3S)-3-methylpiperazin-1-yl]-2-oxoethyl}cyclohexanol. MS (ESI) m/z 337/339 ([M+H]$^+$); HRMS: calcd for $C_{19}H_{29}ClN_2O.2.00$ HCl, 408.1502; found (ESI), 337.202.

Example 5

1-{1-(3-chlorophenyl)-2-[(3R)-3-methylpiperazin-1-yl]ethyl}cyclohexanol dihydrochloride In an analogous manner to Example 1, step 1 1-{1-(3-chlorophenyl)-2-[(3R)-3-methylpiperazin-1-yl]-2-oxoethyl}cyclohexanol was prepared from (3-chlorophenyl)(1-hydroxycyclohexyl)acetic acid (Reference Example 1-a) and (R)-(−)-2-methylpiperazine.

In an analogous manner to Example 1, step 2 1-{1-(3-chlorophenyl)-2-[(3R)-3-methylpiperazin-1-yl]ethyl}cyclohexanol dihydrochloride was prepared from 1-{1-(3-chlorophenyl)-2-[(3 R)-3-methylpiperazin-1-yl]-2-oxoethyl}cyclohexanol. MS (ESI) m/z 337/339 ([M+H]$^+$); HRMS: calcd for $C_{19}H_{29}ClN_2O.2.00$ HCl, 408.1502; found (ESI), 337.2021.

Example 6

1-[1-(3,4-dichlorophenyl)-2-piperazin-1-ylethyl]cyclohexanol dihydrochloride

In an analogous manner to Example 1, step 1 tert-butyl 4-[(3,4-dichlorophenyl)(1-hydroxycyclohexyl)acetyl]piperazine-1-carboxylate was prepared from 3,4-dichloro-alpha-(1-hydroxycyclohexyl)benzeneacetic acid (Reference Example 1-c) and tert-butyl 1-piperazinecarboxylate. HRMS: calcd for $C_{23}H_{32}Cl_2N_2O_4$, 470.1739; found (ESI_FT), 471.18034.

In an analogous manner to Example 1, step 2 1-[1-(3,4-dichlorophenyl)-2-piperazin-1-ylethyl]cyclohexanol dihydrochloride was prepared from tert-butyl 4-[(3,4-dichlorophenyl)(1-hydroxycyclohexyl)acetyl]piperazine-1-carboxylate. MS (ESI) m/z 357/359/361 ([M+H]$^+$); HRMS: calcd for $C_{18}H_{26}Cl_2N_2O.2.00$ HCl, 428.0956; found (ESI_FT), 357.14983.

Example 7

1-[1-(3-bromophenyl)-2-piperazin-1-ylethyl]cycloheptanol dihydrochloride

In an analogous manner to Example 1, step 1 tert-butyl 4-[(3-bromophenyl)(1-hydroxycycloheptyl)acetyl]piperazine-1-carboxylate was prepared from (3-bromophenyl)(1-hydroxycycloheptyl)acetic acid (Reference Example 1-i) and tert-butyl 1-piperazinecarboxylate. MS (ES) m/z 495.3 ([M+H]$^+$).

In an analogous manner to Example 1, step 2 1-[1-(3-bromophenyl)-2-piperazin-1-ylethyl]cycloheptanol dihydrochloride was prepared from tert-butyl 4-[(3-bromophenyl)(1-hydroxycycloheptyl)acetyl]piperazine-1-carboxylate. MS (ES) m/z 381.2 ([M+H]$^+$); HRMS: calcd for $C_{19}H_{29}BrN_2O$.2.00 HCl, 452.0997; found (ESI), 381.1534.

Example 8

1-[1-(3-chlorophenyl)-2-piperazin-1-ylethyl]cycloheptanol dihydrochloride

In an analogous manner to Example 1, step 1 tert-butyl 4-[(3-chlorophenyl)(1-hydroxycycloheptyl)acetyl]piperazine-1-carboxylate was prepared from (3-chlorophenyl)(1-hydroxycycloheptyl)acetic acid (Reference Example 1-j) and tert-butyl 1-piperazinecarboxylate. MS (ES) m/z 451.4 ([M+H]$^+$).

In an analogous manner to Example 1, step 2 1-[1-(3-chlorophenyl)-2-piperazin-1-ylethyl]cycloheptanol dihydrochloride was prepared from tert-butyl 4-[(3-chlorophenyl)(1-hydroxycycloheptyl)acetyl]piperazine-1-carboxylate. MS (ES) m/z 337.2 ([M+H]$^+$); HRMS: calcd for $C_{19}H_{29}ClN_2O$.2.00 HCl, 408.1502; found (ESI), 337.2037.

Example 9

1-[1-(3-fluorophenyl)-2-piperazin-1-ylethyl]cyclohexanol dihydrochloride

In an analogous manner to Example 1, step 1 tert-butyl 4-[(3-fluorophenyl)(1-hydroxycyclohexyl)acetyl]piperazine-1-carboxylate was prepared from (3-fluorophenyl)(1-hydroxycyclohexyl)acetic acid (Reference Example 1-k) and tert-butyl 1-piperazinecarboxylate. HRMS: calcd for $C_{23}H_{33}FN_2O_4$, 420.2424; found (ESI), 421.25.

In an analogous manner to Example 1, step 2 1-[1-(3-fluorophenyl)-2-piperazin-1-ylethyl]cyclohexanol dihydrochloride was prepared from tert-butyl 4-[(3-fluorophenyl)(1-hydroxycyclohexyl)acetyl]piperazine-1-carboxylate. HRMS: calcd for $C_{18}H_{27}FN_2O$.2.00 HCl, 378.1641; found (ESI), 307.2179.

Example 10

1-[1-(3-chlorophenyl)-2-piperazin-1-ylethyl]cyclopentanol dihydrochloride

In an analogous manner to Example 1, step 1 tert-butyl 4-[(3-chlorophenyl)(1-hydroxycyclopentyl)acetyl]piperazine-1-carboxylate was prepared from (3-chlorophenyl)(1-hydroxycyclopentyl)acetic acid (Reference Example 1-y) and tert-butyl 1-piperazinecarboxylate. MS m/z 423/425 ([M+H]$^+$).

In an analogous manner to Example 1, step 2 1-[1-(3-chlorophenyl)-2-piperazin-1-ylethyl]cyclopentanol dihydrochloride was prepared from tert-butyl 4-[(3-chlorophenyl)(1-hydroxycyclopentyl)acetyl]piperazine-1-carboxylate. MS (ESI) m/z 309 ([M+H]$^+$); HRMS: calcd for $C_{17}H_{25}ClN_2O$.2.00 HCl, 380.1189; found (ESI), 309.1744.

Example 11

1-[1-(4-fluorophenyl)-2-piperazin-1-ylethyl]cyclohexanol dihydrochloride

In an analogous manner to Example 1, step 1 tert-butyl 4-[(4-fluorophenyl)(1-hydroxycyclohexyl)acetyl]piperazine-1-carboxylate was prepared from (4-fluorophenyl)(1-hydroxycyclohexyl)acetic acid (Reference Example 1-l) and tert-butyl 1-piperazinecarboxylate. HRMS: calcd for $C_{23}H_{33}FN_2O_4$, 420.2424; found (ESI), 479.2578.

In an analogous manner to Example 1, step 2 1-[1-(4-fluorophenyl)-2-piperazin-1-ylethyl]cyclohexanol dihydrochloride was prepared from tert-butyl 4-[(4-fluorophenyl)(1-hydroxycyclohexyl)acetyl]piperazine-1-carboxylate. HRMS: calcd for $C_{18}H_{27}FN_2O$.2.00 HCl, 378.1641; found (ESI), 307.2166.

Example 12

1-[1-(4-bromophenyl)-2-piperazin-1-ylethyl]cyclobutanol dihydrochloride

In an analogous manner to Example 1, step 1 tert-butyl 4-[(4-bromophenyl)(1-hydroxycyclobutyl)acetyl]piperazine-1-carboxylate was prepared from (4-bromophenyl)(1-hydroxycyclobutyl)acetic acid (Reference Example 1-m) and tert-butyl 1-piperazinecarboxylate.

In an analogous manner to Example 1, step 2 1-[1-(4-bromophenyl)-2-piperazin-1-ylethyl]cyclobutanol dihydrochloride was prepared from tert-butyl 4-[(4-fluorophenyl)(1-hydroxycyclohexyl)acetyl]piperazine-1-carboxylate. MS (ESI) m/z 339 ([M+H]$^+$); HRMS: calcd for $C_{16}H_{23}BrN_2O$.2.00 HCl, 410.0527; found (ESI), 339.

Example 13

1-[1-(3-bromo-4-methoxyphenyl)-2-piperazin-1-ylethyl]cyclopentanol dihydrochloride In an analogous manner to Example 1, step 1 tert-butyl 4-[(3-bromo-4-methoxyphenyl)(1-hydroxycyclopentyl)acetyl]piperazine-1-carboxylate was prepared from (3-bromo-4-methoxyphenyl)(1-hydroxycyclopentyl)acetic acid (Reference Example 1-n) and tert-butyl 1-piperazinecarboxylate. MS (ESI) m/z 497/499 ([M+H]$^+$); HRMS: calcd for $C_{23}H_{33}BrN_2O_5$, 496.1573; found (ESI), 497.1631.

In an analogous manner to Example 1, step 2 1-[1-(3-bromo-4-methoxyphenyl)-2-piperazin-1-ylethyl]cyclopentanol dihydrochloride was prepared from tert-butyl 4-[(3-bromo-4-methoxyphenyl)(1-hydroxycyclopentyl)acetyl]piperazine-1-carboxylate. MS (ESI) m/z 383/385 ([M+H]$^+$); HRMS: calcd for $C_{18}H_{27}BrN_2O_2$.2.00 HCl, 454.0789; found (ESI), 383.1321.

Example 14

1-{2-piperazin-1-yl-1-[3-(trifluoromethyl)phenyl]ethyl}cyclobutanol dihydrochloride In an analogous manner to Example 1, step 1 tert-butyl 4-{(1-hydroxycyclobutyl)[3-(trifluoromethyl)phenyl]acetyl}piperazine-1-carboxylate was prepared (1-hydroxycyclobutyl)[3-(trifluoromethyl)phenyl]acetic acid (Reference Example 1-o) and tert-butyl 1-piperazinecarboxylate. MS (ES) m/z 443.3 ([M+H]$^+$); HRMS: calcd for $C_{22}H_{29}F_3N_2O_4$, 442.2079; found (ESI), 443.2159; Anal. Calcd for $C_{22}H_{29}F_3N_2O_4$: C, 59.72; H, 6.61; N, 6.33. Found: C, 59.98; H, 6.82; N, 6.16.

In an analogous manner to Example 1, step 2 1-{2-piperazin-1-yl-1-[3-(trifluoromethyl)phenyl]ethyl}cyclobutanol dihydrochloride was prepared from tert-butyl 4-{(1-hydroxycyclobutyl)[3-(trifluoromethyl)phenyl]acetyl}piperazine-1-carboxylate. MS (ESI) m/z 329 ([M+H]$^+$); HRMS: calcd for $C_{17}H_{23}F_3N_2O$.2.00 HCl, 400.1296; found (ESI), 329.1815.

Example 15

1-{2-(4-methylpiperazin-1-yl)-1-[3-(trifluoromethyl)phenyl]ethyl}cyclobutanol dihydrochloride A solution of 1-{2-piperazin-1-yl-1-[3-(trifluoromethyl)phenyl]ethyl}cyclobutanol (60 mg, 0.17 mmol), see Example 14, in formic acid (0.33 mL) at 50° C, was treated with an aqueous solution of formaldehyde (37% in water, 0.14 mL, 0.21 mmol). The reaction was heated at 70° C. for 1.5 h, after which time the reaction was poured into water (5 mL) and basified to pH=10 with the addition of a 2 N aqueous solution of sodium hydroxide. The product was then extracted with ethyl acetate (3×4 mL), and the combined organic extracts were dried over magnesium sulfate and concentrated to yield 1-{2-(4-methylpiperazin-1-yl)-1-[3-(trifluoromethyl)phenyl]ethyl}cyclobutanol as a colorless oil. The product was dissolved in methanol (0.5 mL) and the resulting solution was treated with a saturated methanolic solution of hydrochloric acid (0.5 mL) followed by diethyl ether (2 mL). The solution was stored in the refrigerator for 16 h. The resulting precipitate was filtered and washed with diethyl ether to yield 52 mg (69%) 1-{2-(4-methylpiperazin-1-yl)-1-[3-(trifluoromethyl)phenyl]ethyl}cyclobutanol dihydrochloride as a white solid. MS (ESI) m/z 343 ([M+H]$^+$); HRMS: calcd for $C_{18}H_{25}F_3N_2O.2.00$ HCl, 414.1453; found (ESI), 343.2007.

Example 16

1-[1-(3-bromophenyl)-2-piperazin-1-ylethyl]cyclopentanol dihydrochloride

In an analogous manner to Example 1, step 1 tert-butyl 4-[(3-bromophenyl)(1-hydroxycyclopentyl)acetyl]piperazine-1-carboxylate was prepared (3-bromophenyl)(1-hydroxycyclopentyl)acetic acid (Reference Example 1-p) and tert-butyl 1-piperazinecarboxylate. MS (ESI) m/z 467/469 ([M+H]$^+$); HRMS: calcd for $C_{22}H_{31}BrN_2O_4$, 466.1467; found (ESI), 467.1515.

In an analogous manner to Example 1, step 2 1-[1-(3-bromophenyl)-2-piperazin-1-ylethyl]cyclopentanol dihydrochloride was prepared from tert-butyl 4-[(3-bromophenyl)(1-hydroxycyclopentyl)acetyl]piperazine-1-carboxylate. MS (ESI) m/z 353/355 ([M+H]$^+$); HRMS: calcd for $C_{17}H_{25}BrN_2O.2.00$ HCl, 424.0684; found (ESI), 353.1223.

Example 17

1-[1-(4-bromophenyl)-2-piperazin-1-ylethyl]cyclohexanol dihydrochloride

In an analogous manner to Example 1, step 1 tert-butyl 4-[2-(4-bromophenyl)-2-(1-hydroxycyclohexyl)ethyl]piperazine-1-carboxylate was prepared (4-bromophenyl)(1-hydroxycyclohexyl)acetic acid (Reference Example 1-d) and tert-butyl 1-piperazinecarboxylate. MS (ESI) m/z 467/469 ([M+H]$^+$).

In an analogous manner to Example 1, step 2 1-[1-(4-bromophenyl)-2-piperazin-1-ylethyl]cyclohexanol dihydrochloride was prepared from tert-butyl 4-[2-(4-bromophenyl)-2-(1-hydroxycyclohexyl)ethyl]piperazine-1-carboxylate. MS (ESI) m/z 367/369 ([M+H]$^+$); HRMS: calcd for $C_{18}H_{27}BrN_2O.2.00$ HCl, 438.0840; found (ESI), 367.1365.

Example 18

1-[1-(4-chlorophenyl)-2-piperazin-1-ylethyl]cyclobutanol dihydrochloride

In an analogous manner to Example 1, step 1 tert-butyl 4-[(4-chlorophenyl)(1-hydroxycyclobutyl)acetyl]piperazine-1-carboxylate was prepared (4-chlorophenyl)(1-hydroxycyclobutyl)acetic acid (Reference Example 1-q) and tert-butyl 1-piperazinecarboxylate. HRMS: calcd for $C_{21}H_{29}ClN_2O_4$, 408.1816; found (ESI), 409.1878.

In an analogous manner to Example 1, step 2 1-[1-(4-chlorophenyl)-2-piperazin-1-ylethyl]cyclobutanol dihydrochloride was prepared from tert-butyl 4-[(4-chlorophenyl)(1-hydroxycyclobutyl)acetyl]piperazine-1-carboxylate. HRMS: calcd for $C_{16}H_{23}ClN_2O.2.00$ HCl, 366.1032; found (ESI), 295.1556.

Example 19

1-[1-(4-fluorophenyl)-2-piperazin-1-ylethyl]cyclobutanol dihydrochloride

In an analogous manner to Example 1, step 1 tert-butyl 4-[(4-fluorophenyl)(1-hydroxycyclobutyl)acetyl]piperazine-1-carboxylate was prepared (4-fluorophenyl)(1-hydroxycyclobutyl)acetic acid (Reference Example 1-r) and tert-butyl 1-piperazinecarboxylate. HRMS: calcd for $C_{21}H_{29}FN_2O_4$, 392.2111; found (ESI), 393.2187.

In an analogous manner to Example 1, step 2 1-[1-(4-fluorophenyl)-2-piperazin-1-ylethyl]cyclobutanol dihydrochloride was prepared from tert-butyl 4-[(4-chlorophenyl)(1-hydroxycyclobutyl)acetyl]piperazine-1-carboxylate. HRMS: calcd for $C_{16}H_{23}FN_2O.2.00$ HCl, 350.1328; found (ESI), 279.1863.

Example 20

1-[1-(4-bromophenyl)-2-piperazin-1-ylethyl]cyclobutanol dihydrochloride

In an analogous manner to Example 1, step 1 tert-butyl 4-[(4-bromophenyl)(1-hydroxycyclobutyl)acetyl]piperazine-1-carboxylate was prepared (4-bromophenyl)(1-hydroxycyclobutyl)acetic acid (Reference Example 1-m) and tert-butyl 1-piperazinecarboxylate.

In an analogous manner to Example 1, step 2 1-[1-(4-bromophenyl)-2-piperazin-1-ylethyl]cyclobutanol dihydrochloride was prepared from tert-butyl 4-[(4-bromophenyl)(1-hydroxycyclobutyl)acetyl]piperazine-1-carboxylate. MS (ESI) m/z 339 ([M+H]$^+$); HRMS: calcd for $C_{16}H_{23}BrN_2O.2.00$ HCl, 410.0527; found (ESI), 339.

Example 21

1-[1-(4-bromophenyl)-2-(4-methylpiperazin-1-yl)ethyl]cyclobutanol dihydrochloride In an analogous manner to Example 15, 1-[1-(4-bromophenyl)-2-(4-methylpiperazin-1-yl)ethyl]cyclobutanol dihydrochloride was prepared from 1-[1-(4-bromophenyl)-2-piperazin-1-ylethyl]cyclobutanol (see Example 20). MS (ESI) m/z 353/355 ([M+H]$^+$); HRMS: calcd for $C_{17}H_{25}BrN_2O.2.00$ HCl, 424.0684; found (ESI), 353.1205.

Example 22

1-[1-(3-fluorophenyl)-2-piperazin-1-ylethyl]cyclobutanol dihydrochloride

In an analogous manner to Example 1, step 1 tert-butyl 4-[(3-fluorophenyl)(1-hydroxycyclobutyl)acetyl]piperazine-1-carboxylate was prepared (3-fluorophenyl)(1-hydroxycyclobutyl)acetic acid (Reference Example 1-t) and tert-butyl 1-piperazinecarboxylate. HRMS: calcd for $C_{21}H_{29}FN_2O_4$, 392.2111; found (ESI), 393.218.

In an analogous manner to Example 1, step 2 1-[1-(3-fluorophenyl)-2-piperazin-1-ylethyl]cyclobutanol dihydrochloride was prepared from tert-butyl 4-[(3-fluorophenyl)(1-hydroxycyclobutyl)acetyl]piperazine-1-carboxylate. HRMS: calcd for $C_{16}H_{23}FN_2O.2.00$ HCl, 350.1328; found (ESI), 279.1842.

Example 23

1-[1-(3-chlorophenyl)-2-piperazin-1-ylethyl]cyclobutanol dihydrochloride

In an analogous manner to Example 1, step 1 tert-butyl 4-[(3-chlorophenyl)(1-hydroxycyclobutyl)acetyl]piperazine-1-carboxylate was prepared (3-chlorophenyl)(1-hydroxycyclobutyl)acetic acid (Reference Example 1-u) and tert-butyl 1-piperazinecarboxylate. HRMS: calcd for $C_{21}H_{29}FN_2O_4$, 392.2111; found (ESI), 393.218.

In an analogous manner to Example 1, step 2 1-[1-(3-chlorophenyl)-2-piperazin-1-ylethyl]cyclobutanol dihydrochloride was prepared from tert-butyl 4-[(3-chlorophenyl)(1-hydroxycyclobutyl)acetyl]piperazine-1-carboxylate. MS (ESI) m/z [M+H]+ (295/297); HRMS: calcd for $C_{16}H_{23}ClN_2O.2.00$ HCl, 366.1032; found (ESI), 295.1541.

Example 24

1-[1-(3-chlorophenyl)-2-(4-methylpiperazin-1-yl)ethyl]cyclobutanol dihydrochloride

In an analogous manner to Example 15, 1-[1-(3-chlorophenyl)-2-(4-methylpiperazin-1-yl)ethyl]cyclobutanol dihydrochloride was prepared from 1-[1-(3-chlorophenyl)-2-piperazin-1-ylethyl]cyclobutanol (see Example 23). MS (ESI) m/z 309/311 ([M+H]+); HRMS: calcd for $C_{17}H_{25}ClN_2O.2.00$ HCl, 380.1189; found (ESI), 309.1711.

Example 25

1-[1-(2-fluorophenyl)-2-piperazin-1-ylethyl]cyclohexanol dihydrochloride

In an analogous manner to Example 1, step 1 tert-butyl 4-[(2-fluorophenyl)(1-hydroxycyclohexyl)acetyl]piperazine-1-carboxylate was prepared (2-fluorophenyl)(1-hydroxycyclohexyl)acetic acid (Reference Example 1-v) and tert-butyl 1-piperazinecarboxylate. HRMS: calcd for $C_{21}H_{29}FN_2O_4$, 392.2111; found (ESI), 393.218. MS (ESI) m/z 421 ([M+H]+); HRMS: calcd for $C_{23}H_{33}FN_2O_4$, 420.2424; found (ESI), 421.2509; Anal. Calcd for $C_{23}H_{33}FN_2O_4$: C, 65.69; H, 7.91; N, 6.66. Found: C, 65.77; H, 7.95; N, 6.63.

In an analogous manner to Example 1, step 2 1-[1-(2-fluorophenyl)-2-piperazin-1-ylethyl]cyclohexanol dihydrochloride was prepared from tert-butyl 4-[(2-fluorophenyl)(1-hydroxycyclohexyl)acetyl]piperazine-1-carboxylate. MS (ESI) m/z 307 ([M+H]+); HRMS: calcd for $C_{18}H_{27}FN_2O.2.00$ HCl, 378.1641; found (ESI), 307.2156.

Example 26

1-[1-(4-chlorophenyl)-2-piperazin-1-ylethyl]cyclohexanol dihydrochloride

In an analogous manner to Example 1, step 1 tert-butyl 4-[(4-chlorophenyl)(1-hydroxycyclohexyl)acetyl]piperazine-1-carboxylate was prepared (4-chlorophenyl)(1-hydroxycyclohexyl)acetic acid (Reference Example 1-w) and tert-butyl 1-piperazinecarboxylate. HRMS: calcd for $C_{23}H_{33}ClN_2O_4$, 436.2129; found (ESI), 437.2213.

In an analogous manner to Example 1, step 2 1-[1-(4-chlorophenyl)-2-piperazin-1-ylethyl]cyclohexanol dihydrochloride was prepared from tert-butyl 4-[(4-chlorophenyl)(1-hydroxycyclohexyl)acetyl]piperazine-1-carboxylate. HRMS: calcd for $C_{18}H_{27}ClN_2O.2.00$ HCl, 394.1345; found (ESI), 323.1868.

Example 27

1-[1-(3-bromophenyl)-2-piperazin-1-ylethyl]cyclobutanol dihydrochloride

In an analogous manner to Example 1, step 1 tert-butyl 4-[(3-bromophenyl)(1-hydroxycyclobutyl)acetyl]piperazine-1-carboxylate was prepared (3-bromophenyl)(1-hydroxycyclobutyl)acetic acid (Reference Example 1-e) and tert-butyl 1-piperazinecarboxylate. HRMS: calcd for $C_{21}H_{29}BrN_2O_4$, 452.1311; found (ESI_FT), 453.13746.

In an analogous manner to Example 1, step 2 1-[1-(3-bromophenyl)-2-piperazin-1-ylethyl]cyclobutanol dihydrochloride was prepared from tert-butyl 4-[(3-bromophenyl)(1-hydroxycyclobutyl)acetyl]piperazine-1-carboxylate. HRMS: calcd for $C_{16}H_{23}BrN_2O.2.00$ HCl, 410.0527; found (ESI_FT), 339.10725.

Example 28

1-[1-(2-fluorophenyl)-2-piperazin-1-ylethyl]cyclobutanol dihydrochloride

In an analogous manner to Example 1, step 1 tert-butyl 4-[(2-fluorophenyl)(1-hydroxycyclobutyl)acetyl]piperazine-1-carboxylate was prepared (2-fluorophenyl)(1-hydroxycyclobutyl)acetic acid (Reference Example 1-x) and tert-butyl 1-piperazinecarboxylate. MS (ESI) m/z 393 ([M+H]+); HRMS: calcd for $C_{21}H_{29}FN_2O_4$, 392.2111; found (ESI), 393.2182; Anal. Calcd for $C_{21}H_{29}FN_2O_4$: C, 64.27; H, 7.45; N, 7.14. Found: C, 63.89; H, 7.43; N, 6.99.

In an analogous manner to Example 1, step 2 1-[1-(2-fluorophenyl)-2-piperazin-1-ylethyl]cyclobutanol dihydrochloride was prepared from tert-butyl 4-[(2-fluorophenyl)(1-hydroxycyclobutyl)acetyl]piperazine-1-carboxylate. MS (ESI) m/z 351 ([M+H]+); HRMS: calcd for $C_{16}H_{23}FN_2O.2.00$ HCl, 350.1328; found (ESI), 279.1872.

Example 29

1-[1-(3-fluorophenyl)-2-(4-methylpiperazin-1-yl)ethyl]cyclobutanol dihydrochloride

In an analogous manner to Example 15, 1-[1-(3-fluorophenyl)-2-(4-methylpiperazin-1-yl)ethyl]cyclobutanol dihydrochloride was prepared from 1-[1-(3-fluorophenyl)-2-piperazin-1-ylethyl]cyclobutanol (see Example 22). HRMS: calcd for $C_{17}H_{25}FN_2O.2.00$ HCl, 364.1484; found (ESI), 293.1999.

Example 30

1-[1-(4-chlorophenyl)-2-(4-methylpiperazin-1-yl) ethyl]cyclobutanol dihydrochloride In an analogous manner to Example 15, 1-[1-(4-chlorophenyl)-2-(4-methylpiperazin-1-yl)ethyl]cyclobutanol dihydrochloride was prepared from 1-[1-(4-chlorophenyl)-2-piperazin-1-ylethyl]cyclobutanol (see Example 18). HRMS: calcd for $C_{17}H_{25}ClN_2O.2.00$ HCl, 380.1189; found (ESI), 309.1717.

Example 31

1-[1-(2-fluorophenyl)-2-(4-methylpiperazin-1-yl) ethyl]cyclobutanol dihydrochloride In an analogous manner to Example 15, 1-[1-(2-fluorophenyl)-2-(4-methylpiperazin-1-yl)ethyl]cyclobutanol dihydrochloride was prepared from 1-[1-(2-fluorophenyl)-2-piperazin-1-ylethyl]cyclobutanol (see Example 28). MS (ESI) m/z 293 ([M+H]$^+$); HRMS: calcd for $C_{17}H_{25}FN_2O.2.00$ HCl, 364.1484; found (ESI), 293.2015.

Example 32

1-[1-(4-fluorophenyl)-2-(4-methylpiperazin-1-yl) ethyl]cyclobutanol dihydrochloride In an analogous manner to Example 15, 1-[1-(4-fluorophenyl)-2-(4-methylpiperazin-1-yl)ethyl]cyclobutanol dihydrochloride was prepared from 1-[1-(4-fluorophenyl)-2-piperazin-1-ylethyl]cyclohexanol (see Example 11). HRMS: calcd for $C_{17}H_{25}FN_2O.2.00$ HCl, 364.1484; found (ESI), 293.1999.

Example 33

1-[1-(2-bromophenyl)-2-piperazin-1-ylethyl]cyclohexanol dihydrochloride

In an analogous manner to Example 1, step 1 tert-butyl 4-[(2-bromophenyl)(1-hydroxycyclohexyl)acetyl]piperazine-1-carboxylate was prepared (2-bromophenyl)(1-hydroxycyclohexyl)acetic acid (Reference Example 1-s) and tert-butyl 1-piperazinecarboxylate. MS (ESI) m/z 481/483 ([M+H]$^+$); HRMS: calcd for $C_{23}H_{33}BrN_2O_4$, 480.1624; found (ESI), 481.1689.

In an analogous manner to Example 1, step 2 1-[1-(2-bromophenyl)-2-piperazin-1-ylethyl]cyclohexanol dihydrochloride was prepared from tert-butyl 4-[(2-bromophenyl)(1-hydroxycyclohexyl)acetyl]piperazine-1-carboxylate. MS (ESI) m/z 367/369 ([M+H]$^+$); HRMS: calcd for $C_{18}H_{27}BrN_2O.2.00$ HCl, 438.0840; found (ESI), 367.1385.

Example 34

1-[(1S)-1-(3-chlorophenyl)-2-piperazin-1-ylethyl] cyclohexanol dihydrochloride

Racemic tert-butyl 4-[(3-chlorophenyl)(1-hydroxycyclohexyl)acetyl]piperazine-1-carboxylate (see Example 1, step 1) was dissolved in methanol at a concentration of approximately 50 mg/mL. The resulting solution was injected onto the Supercritical Fluid Chromatography instrument with an injection volume of 750 □L. The baseline resolved enantiomers, using the conditions described below, were collected. The enantiomeric purity of each enantiomer was determined under the same Supercritical Fluid Chromatography conditions using a Chiralpak AD-H 5 u, 250 mm×4.6 mm ID column at 2.0 mL/min flow rate using Analytical Supercritical Fluid Chromatography (Berger Instruments, Inc. Newark, Del. USA).

| | |
|---|---|
| SFC Instrument: | Berger MultiGram PrepSFC (Berger Instruments, Inc. Newark, DE 19702. |
| Column: | Chiralpak AD-H; 5u; 250 mm L × 20 mm ID (Chiral Technologies, Inc, Exton, PA, USA) |
| Column temperature: | 35° C. |
| SFC Modifier: | 40% MeOH |
| Flow rate: | 50 mL/min |
| Outlet Pressure: | 100 bar |
| Detector: | UV at 220 nm | tert-butyl 4-[(2S)-2-(3-chlorophenyl)-2-(1-hydroxycyclohexyl)acetyl]piperazine-1-carboxylate was isolated at peak 1. HRMS: calcd for $C_{23}H_{33}ClN_2O_4$, 436.2129; found (ESI), 495.2272; $[\alpha]_D^{25}$=+14.0° (c=0.0062 G/ML, EtOH).

tert-butyl 4-[(2R)-2-(3-chlorophenyl)-2-(1-hydroxycyclohexyl)acetyl]piperazine-1-carboxylate was isolated at peak 2. HRMS: calcd for $C_{23}H_{33}ClN_2O_4$, 436.2129; found (ESI), 437.2203; ; $[\alpha]_D^{25}$=−24° (c=0.0046 G/ML, EtOH).

In an analogous manner to Example 1, step 2 1-[(1S)-1-(3-chlorophenyl)-2-piperazin-1-ylethyl]cyclohexanol dihydrochloride was prepared from tert-butyl 4-[(2R)-2-(3-chlorophenyl)-2-(1-hydroxycyclohexyl)acetyl]piperazine-1-carboxylate. MS (ESI) m/z 323/325 ([M+H]$^+$); HRMS: calcd for $C_{18}H_{27}ClN_2O.2.00$ HCl, 394.1345; found (ESI), 323.1867; $[\alpha]_D^{25}$=+12.5° (c=0.0049 G/ML, EtOH).

Example 35

1-[(1R)-1-(3-chlorophenyl)-2-piperazin-1-ylethyl] cyclohexanol dihydrochloride

In an analogous manner to Example 1, step 2 1-[(1R)-1-(3-chlorophenyl)-2-piperazin-1-ylethyl]cyclohexanol dihydrochloride was prepared from tert-butyl 4-[(2S)-2-(3-chlorophenyl)-2-(1-hydroxycyclohexyl)acetyl]piperazine-1-carboxylate (see Example 34). MS (ESI) m/z 323/325 ([M+H]$^+$); HRMS: calcd for $C_{18}H_{27}ClN_2O.2.00$ HCl, 394.1345; found (ESI), 323.1873; $[\alpha]_D^{25}$=−7.0° (c=0.0051 G/ML, EtOH).

Example 36

1-[1-(3-chlorophenyl)-2-piperazin-1-ylethyl]cyclooctanol dihydrochloride

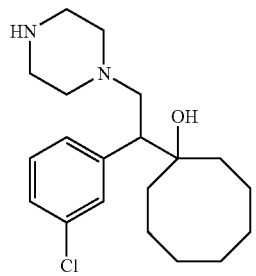

In an analogous manner to Example 1, step 1 tert-butyl 4-[(3-chlorophenyl)(1-hydroxycyclooctyl)acetyl]piperazine-1-carboxylate was prepared from (3-chlorophenyl)(1-hydroxycyclooctyl)acetic acid (Reference Example 1-aa) and tert-butyl 1-piperazinecarboxylate. MS (ESI) m/z 465.

In an analogous manner to Example 1, step 2 1-[1-(3-chlorophenyl)-2-piperazin-1-ylethyl]cyclooctanol dihydrochloride was prepared from tert-butyl 4-[(3-chlorophenyl)(1-hydroxycyclooctyl)acetyl]piperazine-1-carboxylate. MS (ES) m/z 351.2; HRMS: calcd for $C_{20}H_{31}ClN_2O+H$, 351.22031; found (ESI, [M+H]+), 351.2191.

Example 37

1-[1-(3-bromophenyl)-2-piperazin-1-ylethyl]cyclooctanol dihydrochloride

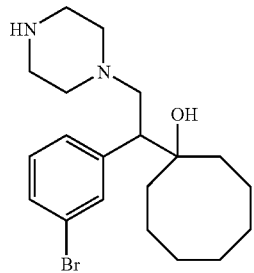

In an analogous manner to Example 1, step 1 tert-butyl 4-[(3-bromophenyl)(1-hydroxycyclooctyl)acetyl]piperazine-1-carboxylate was prepared from (3-bromophenyl)(1-hydroxycyclooctyl)acetic acid (Reference Example 1-bb) and tert-butyl 1-piperazinecarboxylate. MS (ESI) m/z 509.

In an analogous manner to Example 1, step 2 1-[1-(3-bromophenyl)-2-piperazin-1-ylethyl]cyclooctanol dihydrochloride was prepared from tert-butyl 4-[(3-bromophenyl)(1-hydroxycyclooctyl)acetyl]piperazine-1-carboxylate. MS m/z 395; HRMS: calcd for $C_{20}H_{31}BrN_2O+H$, 395.16980; found (ESI, [M+H]+), 395.1686.

Example 38

1-[1-(3-bromo-4-methoxyphenyl)-2-piperazin-1-ylethyl]cyclooctanol dihydrochloride

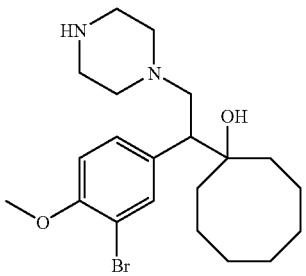

In an analogous manner to Example 1, step 1 tert-butyl 4-[(3-bromo-4-methoxyphenyl)(1-hydroxycyclooctyl)acetyl]piperazine-1-carboxylate was prepared from (3-bromo-4-methoxyphenyl)(1-hydroxycyclooctyl)acetic acid (Reference Example 1-cc) and tert-butyl 1-piperazinecarboxylate. MS (ESI) m/z 539.

In an analogous manner to Example 1, step 2 1-[1-(3-bromo-4-methoxyphenyl)-2-piperazin-1-ylethyl]cyclooctanol dihydrochloride was prepared from tert-butyl 4-[(3-bromo-4-methoxyphenyl)(1-hydroxycyclooctyl)acetyl]piperazine-1-carboxylate. MS (ESI) m/z 425; HRMS: calcd for $C_{21}H_{33}BrN_2O_2 \cdot 2.00$ HCl, 496.1259; found (ESI, [M+H]+), 425.1801.

Example 39

1-[1-(3-chlorophenyl)-2-(4-methylpiperazin-1-yl)ethyl]cyclooctanol dihydrochloride

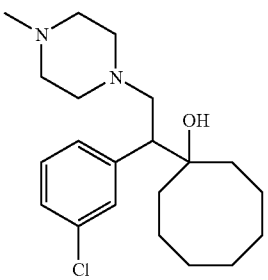

In an analogous manner to Example 24, 1-[1-(3-chlorophenyl)-2-(4-methylpiperazin-1-yl)ethyl]cyclooctanol dihydrochloride was prepared from 1-[1-(3-chlorophenyl)-2-piperazin-1-ylethyl]cyclooctanol (see Example 36). MS (ESI) m/z 365; HRMS: calcd for $C_{21}H_{33}ClN_2O+H$, 365.23597; found (ESI, [M+H]+), 365.235.

Example 40

1-[1-(3-bromophenyl)-2-(4-methylpiperazin-1-yl)ethyl]cyclooctanol dihydrochloride

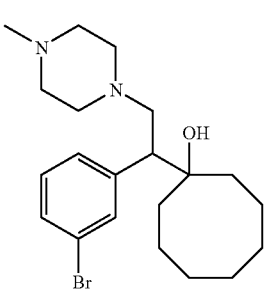

In an analogous manner to Example 24, 1-[1-(3-bromophenyl)-2-(4-methylpiperazin-1-yl)ethyl]cyclooctanol dihydrochloride was prepared from 1-[1-(3-bromophenyl)-2-piperazin-1-ylethyl]cyclooctanol (see Example 37). MS (ESI) m/z 409; HRMS: calcd for $C_{21}H_{33}BrN_2O+H$, 409.18545; found (ESI, [M+H]+), 409.1856.

Example 41

1-[1-(3-bromo-4-methoxyphenyl)-2-(4-methylpiperazin-1-yl)ethyl]cyclooctanol dihydrochloride

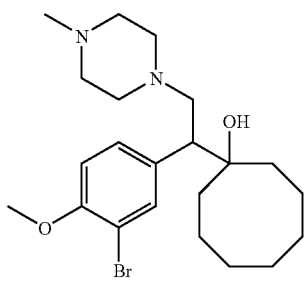

In an analogous manner to Example 24, 1-[1-(3-bromo-4-methoxyphenyl)-2-(4-methylpiperazin-1-yl)ethyl]cyclooctanol dihydrochloride was prepared from 1-[1-(3-bromo-4-methoxyphenyl)-2-piperazin-1-ylethyl]cyclooctanol (see Example 38). MS (ESI) m/z 439; HRMS: calcd for $C_{22}H_{35}BrN_2O_2+H$, 439.19601; found (ESI, [M+H]+), 439.1961.

Cell Lines, Culture Reagents, and Assays

MDCK-Net6 cells, stably transfected with human hNET (Pacholczyk, T., R. D. Blakely, and S. G. Amara, *Nature*, 1991, 350(6316): p. 350-4) were cultured in growth medium containing high glucose DMEM (Gibco, Cat. No. 11995), 10% FBS (dialyzed, heat-inactivated, US Bio-Technologies, Lot FBD1129HI) and 500 □g/ml G418 (Gibco, Cat. No. 10131). Cells were plated at 300,000/T75 flask and cells were split twice weekly. The JAR cell line (human placental choriocarcinoma) was purchased from ATCC (Cat. No. HTB-144). The cells were cultured in growth medium containing RPMI 1640 (Gibco, Cat. No. 72400), 10% FBS (Irvine, Cat. No. 3000), 1% sodium pyruvate (Gibco, Cat. No. 1136) and 0.25% glucose. Cells were plated at 250,000 cells/T75 flask and split twice weekly. For all assays, cells were plated in Wallac 96-well sterile plates (PerkinElmer, Cat. No. 3983498).

Norepinephrine (NE) Uptake Assay

On day 1, cells were plated at 3,000 cells/well in growth medium and maintained in a cell incubator (37° C., 5% CO$_2$). On day 2, growth medium was replaced with 200 µl of assay buffer (25 mM HEPES; 120 mM NaCl; 5 mM KCl; 2.5 mM CaCl$_2$; 1.2 mM MgSO$_4$; 2 mg/ml glucose (pH 7.4, 37° C.)) containing 0.2 mg/ml ascorbic acid and 10 µM pargyline. Plates containing cells with 200 µl of assay buffer were equilibrated for 10 minutes at 37° C. prior to addition of compounds. A stock solution of desipramine was prepared in DMSO (10 mM) and delivered to triplicate wells containing cells for a final test concentration of 1 µM. Data from these wells were used to define non-specific NE uptake (minimum NE uptake). Test compounds were prepared in DMSO (10 mM) and diluted in assay buffer according to test range (1 to 10,000 nM). Twenty-five microliters of assay buffer (maximum NE uptake) or test compound were added directly to triplicate wells containing cells in 200 µl of assay buffer. The cells in assay buffer with test compounds were incubated for 20 minutes at 37° C. To initiate the NE uptake, [$^3$H]NE diluted in assay buffer (120 nM final assay concentration) was delivered in 25 µl aliquots to each well and the plates were incubated for 5 minutes (37° C.). The reaction was terminated by decanting the supernatant from the plate. The plates containing cells were washed twice with 200 µl assay buffer (37° C.) to remove free radioligand. The plates were then inverted, left to dry for 2 minutes, then reinverted and air-dried for an additional 10 minutes. The cells were lysed in 25 µl of 0.25 N NaOH solution (4° C.), placed on a shake table and vigorously shaken for 5 minutes. After cell lysis, 75 µl of scintillation cocktail was added to each well and the plates were sealed with film tape. The plates were returned to the shake table and vigorously shaken for a minimum of 10 minutes to ensure adequate partitioning of organic and aqueous solutions. The plates were counted in a Wallac Microbeta counter (PerkinElmer) to collect the raw cpm data.

Serotonin (5-HT) Uptake Assay

The methods for 5-HT functional reuptake using the JAR cell line were modified using a previous literature report (Prasad, et al., *Placenta*, 1996. 17(4): 201-7). On day 1, cells were plated at 15,000 cells/well in 96-well plates containing growth medium (RPMI 1640 with 10% FBS) and maintained in a cell incubator (37° C., 5% CO$_2$). On day 2, cells were stimulated with staurosporine (40 nM) to increase the expression of the 5-HT transporter [17]. On day 3, cells were removed from the cell incubator two hours prior to assay and maintained at room temperature to equilibrate the growth medium to ambient oxygen concentration. Subsequently, the growth medium was replaced with 200 µl of assay buffer (25 mM HEPES; 120 mM NaCl; 5 mM KCl; 2.5 mM CaCl$_2$; 1.2 mM MgSO$_4$; 2 mg/ml glucose (pH 7.4, 37° C.)) containing 0.2 mg/ml ascorbic acid and 10 µM pargyline. A stock solution of paroxetine (AHR-4389-1) was prepared in DMSO (10 mM) and delivered to triplicate wells containing cells for a final test concentration of 1 µM. Data from these wells were used to define non-specific 5-HT uptake (minimum 5-HT uptake). Test compounds were prepared in DMSO (10 mM) and diluted in assay buffer according to test range (1 to 1,000 nM). Twenty-five microliters of assay buffer (maximum 5-HT uptake) or test compound were added directly to triplicate wells containing cells in 200 µl of assay buffer. The cells were incubated with the compound for 10 minutes (37° C.). To initiate the reaction, [$^3$H]hydroxytryptamine creatinine sulfate diluted in assay buffer was delivered in 25 µl aliquots to each well for a final test concentration of 15 nM. The cells were incubated with the reaction mixture for 5 minutes at 37° C. The 5-HT uptake reaction was terminated by decanting the assay buffer. The cells were washed twice with 200 µl assay buffer (37° C.) to remove free radioligand. The plates were inverted and left to dry for 2 minutes, then reinverted and air-dried for an additional 10 minutes. Subsequently, the cells were lysed in 25 µl of 0.25 N NaOH (4° C.) then placed on a shaker table and shaken vigorously for 5 minutes. After cell lysis, 75 µl of scintillation cocktail was added to the wells, the plates were sealed with film tape and replaced on the shake table for a minimum of 10 minutes. The plates were counted in a Wallac Microbeta counter (PerkinElmer) to collect the raw cpm data.

Evaluation of Results

For each experiment, a data stream of cpm values collected from the Wallac Microbeta counter was downloaded to a Microsoft Excel statistical application program. Calculations of $EC_{50}$ values were made using the transformed-both-sides logistic dose response program written by Wyeth Biometrics Department. The statistical program uses mean cpm values from wells representing maximum binding or uptake (assay buffer) and mean cpm values from wells representing minimum binding or uptake ((1 µM desipramine (hNET) or 1 µM paroxetine (hSERT)). Estimation of the $EC_{50}$ value was completed on a log scale and the line was fit between the maximum and minimum binding or uptake values. All graphic data representation was generated by normalizing each data point to a mean percent based on the maximum and minimum binding or uptake values. The $EC_{50}$ values reported from multiple experiments were calculated by pooling the raw data from each experiment and analyzing the pooled data as one experiment.

The results are reported in Table 1.

TABLE 1

| Example | % Inhibition @ 1 µM (hNET) | hNET $EC_{50}$ (nM) |
|---|---|---|
| 1 | 93 | 18 |
| 2 | 97 | 150 |
| 3 | 96 | 100 |
| 4 | 95 | 59 |
| 5 | 94 | 110 |
| 6 | 87 | 210 |
| 7 | 86 | |
| 8 | 81 | |
| 9 | 79 | 720 |
| 10 | 63 | |
| 11 | 60 | 6400 |
| 12 | 55 | |
| 13 | 53 | |
| 14 | 27 | |
| 15 | 51 | |
| 16 | 51 | |
| 17 | 46 | |
| 18 | 44 | |
| 19 | 43 | |
| 20 | 55 | |
| 21 | 36 | |
| 22 | 34 | |
| 23 | 28 | |
| 24 | 34 | |
| 25 | 31 | |
| 26 | 29 | |
| 27 | 22 | |
| 28 | 14 | |
| 29 | 12 | |
| 30 | −1 | |
| 31 | −6 | |
| 32 | −10 | |
| 33 | 35 | |
| 34 | | 25 |
| 35 | | 540 |
| 36 | 28 | |
| 37 | 28 | |
| 38 | 42 | |
| 39 | 42 | |
| 40 | 44 | |
| 41 | 48 | |

When ranges are used herein for physical properties, such as molecular weight, or chemical properties, such as chemical formulae, all combinations and subcombinations of ranges specific embodiments therein are intended to be included.

The disclosures of each patent, patent application and publication cited or described in this document are hereby incorporated herein by reference, in its entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variation as fall within the true spirit and scope of the invention.

What is claimed is:

1. A compound of formula I:

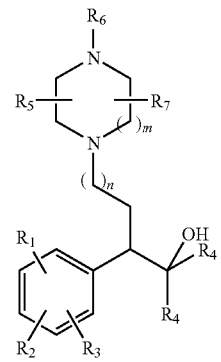

or a pharmaceutically acceptable salt thereof;
wherein:
$R^1$, $R^2$ and $R^3$ are, independently, H, OH, alkyl, alkoxy, alkanoyloxy, $CF_3$, or halo;
or any two of $R^1$, $R^2$ and $R^3$ taken together are methylenedioxy;
both $R^4$, taken together with the carbon atom to which they are attached, form a cyclobutyl, cyclopentyl, cycloheptyl, or cyclooctyl ring;
$R^5$, $R^6$, and $R^7$ are, independently, H or $(C_1$-$C_4)$alkyl, provided that at least one of $R^5$, $R^6$, and $R^7$ is other than H;
m is 1 or 3;
and n is 0, 1, 2, or 3.

2. A compound according to claim 1, wherein $R^1$ is halogen, methoxy, and trifluoromethyl.

3. A compound according to claim 1, wherein $R^2$ is hydrogen, halogen, methoxy, or trifluoromethyl.

4. A compound according to claim 1, wherein $R^3$ is hydrogen.

5. A compound according to claim 1, wherein n is 0.

6. A compound according to claim 1, wherein $R^5$ and $R^7$ are each selected from hydrogen and methyl.

7. A compound according to claim 1, wherein $R^6$ is hydrogen or methyl.

8. A compound according to claim 1, wherein n is 0 and which is the 1 S-enantiomer.

9. A compound, wherein said compound is:
1-[1-(3-chlorophenyl)-2-piperazin-1-ylethyl]cyclohexanol;
1-{1-(3-chlorophenyl)-2-[(3R,5S)-3,5-dimethylpiperazin-1-yl]ethyl}cyclohexanol;
1-[1-(3-bromophenyl)-2-piperazin-1-ylethyl]cyclohexanol
1-{1-(3-chlorophenyl)-2-[(3S)-3-methylpiperazin-1-yl]ethyl}cyclohexanol;

1-{1-(3-chlorophenyl)-2-[(3R)-3-methylpiperazin-1-yl]ethyl}cyclohexanol;
1-[1-(3,4-dichlorophenyl)-2-piperazin-1-ylethyl]cyclohexanol;
1-[1-(3-bromophenyl)-2-piperazin-1-ylethyl]cycloheptanol;
1-[1-(3-chlorophenyl)-2-piperazin-1-ylethyl]cycloheptanol;
1-[1-(3-fluorophenyl)-2-piperazin-1-ylethyl]cyclohexanol;
1-[1-(3-chlorophenyl)-2-piperazin-1-ylethyl]cyclopentanol;
1-[1-(4-fluorophenyl)-2-piperazin-1-ylethyl]cyclohexanol;
1-[1-(4-bromophenyl)-2-piperazin-1-ylethyl]cyclobutanol;
1-[1-(3-bromo-4-methoxyphenyl)-2-piperazin-1-ylethyl]cyclopentanol;
1-{2-piperazin-1-yl-1-[3-(trifluoromethyl)phenyl]ethyl}cyclobutanol;
1-[1-(3-bromophenyl)-2-piperazin-1-ylethyl]cyclopentanol;
1-[1-(4-bromophenyl)-2-piperazin-1-ylethyl]cyclohexanol;
1-[1-(4-chlorophenyl)-2-piperazin-1-ylethyl]cyclobutanol;
1-[1-(4-fluorophenyl)-2-piperazin-1-ylethyl]cyclobutanol;
1-[1-(4-bromophenyl)-2-piperazin-1-ylethyl]cyclobutanol;
1-[1-(3-fluorophenyl)-2-piperazin-1-ylethyl]cyclobutanol;
1-[1-(3-chlorophenyl)-2-piperazin-1-ylethyl]cyclobutanol;
1-[1-(2-fluorophenyl)-2-piperazin-1-ylethyl]cyclohexanol;
1-[1-(4-chlorophenyl)-2-piperazin-1-ylethyl]cyclohexanol;
1-[1-(3-bromophenyl)-2-piperazin-1-ylethyl]cyclobutanol;
1-[1-(2-fluorophenyl)-2-piperazin-1-ylethyl]cyclobutanol;
1-[1-(2-bromophenyl)-2-piperazin-1-ylethyl]cyclohexanol;
1-[(1S)-1-(3-chlorophenyl)-2-piperazin-1-ylethyl]cyclohexanol;
1-[(1R)-1-(3-chlorophenyl)-2-piperazin-1-ylethyl]cyclohexanol;
1-[1-(3-chlorophenyl)-2-piperazin-1-ylethyl]cyclooctanol;
1-[1-(3-bromophenyl)-2-piperazin-1-ylethyl]cyclooctanol;
1-[1-(3-bromo-4-methoxyphenyl)-2-piperazin-1-ylethyl]cyclooctanol;
or a pharmaceutically acceptable salt thereof.

10. A compound according to claim 1, wherein said compound is in the form of the dihydrochloride salt.

11. A composition, comprising:
a. at least one compound according to claim 1; and
b. at least one pharmaceutically acceptable carrier.

12. A compound of formula I:

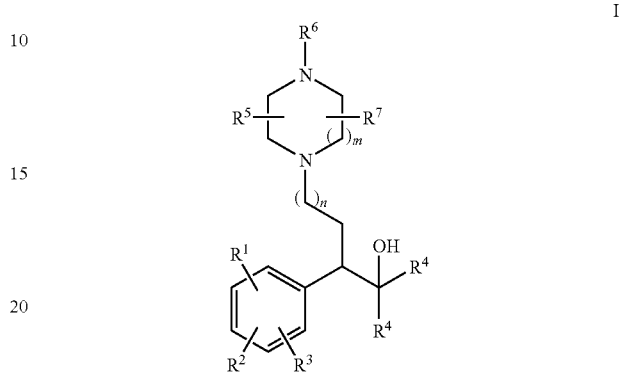

or a pharmaceutically acceptable salt thereof;
wherein: $R^1$, $R^2$ and $R^3$ are, independently, H, OH, alkyl, alkoxy, alkanoyloxy, $CF_3$, or halo;
or any two of $R^1$, $R^2$ and $R^3$ taken together are methylenedioxy;
$R^4$, taken together with the carbon atom to which they are attached, form a cycloalkyl ring of 4 to 8 carbon atoms;
$R^5$ is H or $(C_1$-$C_4)$alkyl;
$R^6$ is H;
$R^7$ is H or $(C_1$-$C_4)$alkyl, provided that at least one of $R^5$, and $R^7$ is other than H;
m is 1, 2, or 3;
and n is 0, 1, 2, or 3.

13. A compound according to claim 12, wherein $R^1$ is halogen, methoxy, and trifluoromethyl.

14. A compound according to claim 12, wherein $R^2$ is hydrogen, halogen, methoxy, or trifluoromethyl.

15. A compound according to claim 12, wherein $R^3$ is hydrogen.

16. A compound according to claim 12, wherein n is 0.

17. A compound according to claim 12, wherein m is 1.

18. A compound according to claim 12, wherein $R^6$ and $R^7$ are each selected from hydrogen and methyl.

19. A compound according to claim 12, wherein n is 0 and which is the 1 S-enantiomer.

20. A composition, comprising:
a. at least one compound according to claim 12; and
b. at least one pharmaceutically acceptable carrier.

* * * * *